US012740759B2

(12) United States Patent
Bajikar et al.

(10) Patent No.: US 12,740,759 B2
(45) Date of Patent: Sep. 22, 2026

(54) MULTIPLE APERTURE ULTRASOUND IMAGING SYSTEMS AND METHODS

(71) Applicant: Maui Imaging, Inc., San Jose, CA (US)

(72) Inventors: Sateesh Bajikar, San Jose, CA (US); Elias M. Atmeh, San Jose, CA (US); Bruce R. Ritzi, Sunnyvale, CA (US); David J. Specht, San Jose, CA (US)

(73) Assignee: Maui Imaging, Inc., San Jose, CA (US)

( * ) Notice: Subject to any disclaimer, the term of this patent is extended or adjusted under 35 U.S.C. 154(b) by 311 days.

(21) Appl. No.: 18/165,276

(22) Filed: Feb. 6, 2023

(65) Prior Publication Data

US 2023/0248333 A1 Aug. 10, 2023

Related U.S. Application Data

(60) Provisional application No. 63/306,936, filed on Feb. 4, 2022.

(51) Int. Cl.
*A61B 8/14* (2006.01)
*A61B 8/00* (2006.01)
(Continued)

(52) U.S. Cl.
CPC ............ *A61B 8/145* (2013.01); *A61B 8/0841* (2013.01); *A61B 8/4455* (2013.01);
(Continued)

(58) Field of Classification Search
CPC ..... A61B 8/145; A61B 8/0841; A61B 8/4455; A61B 8/4488
See application file for complete search history.

(56) References Cited

U.S. PATENT DOCUMENTS 3,174,286 A 3/1965 Erickson
3,895,381 A 7/1975 Kock
(Continued)

FOREIGN PATENT DOCUMENTS

CN 1535243 A 10/2004
CN 1636150 A 7/2005
(Continued)

OTHER PUBLICATIONS

Lockwood et al.; Real-time 3-D ultrasound imaging using sparse synthetic aperture beamforming; IEEE transactions on ultrasonics, ferroelectrics, and frequency control; 45(4); pp. 980-988; Jul. 1998.
(Continued)

*Primary Examiner* — Baisakhi Roy
(74) *Attorney, Agent, or Firm* — Shay Glenn LLP

(57) ABSTRACT

Systems and methods of ultrasound imaging are provided. In some embodiments, unfocused and diverging ultrasound signals can be transmitted into a target medium from an apparent point source located aft of a concave probe surface. The echoes can be received, and a location of a reflector within the target medium can be determined. The location can be determined by obtaining element position data describing a position of the spherical center point of the apparent point source r and a position of the receive element, calculating a total path distance as a sum of a first distance between the spherical center point and the reflector and a second distance between the reflector and the receive element, and determining a locus of possible points at which the reflector may lie. A data set can then be produced for the entire target medium.

12 Claims, 15 Drawing Sheets

(51) Int. Cl.
*A61B 8/08* (2006.01)
*G01S 15/89* (2006.01)

(52) U.S. Cl.
CPC ........ *A61B 8/4488* (2013.01); *G01S 15/8913* (2013.01); *G01S 15/8918* (2013.01); *G01S 15/892* (2013.01); *G01S 15/8925* (2013.01); *G01S 15/8934* (2013.01); *G01S 15/8997* (2013.01)

(56) References Cited

U.S. PATENT DOCUMENTS 3,974,692 A 8/1976 Hassler
4,055,988 A 11/1977 Dutton
4,072,922 A 2/1978 Taner et al.
4,097,835 A 6/1978 Green
4,105,018 A 8/1978 Greenleaf et al.
4,180,792 A 12/1979 Lederman et al.
4,205,394 A 5/1980 Pickens
4,229,798 A 10/1980 Rosie
4,259,733 A 3/1981 Taner et al.
4,265,126 A 5/1981 Papadofrangakis et al.
4,271,842 A 6/1981 Specht et al.
4,325,257 A 4/1982 Kino et al.
4,327,738 A 5/1982 Green et al.
4,328,569 A 5/1982 Trott et al.
4,333,474 A 6/1982 Nigam
4,339,952 A 7/1982 Foster
4,452,084 A 6/1984 Taenzer
4,501,279 A 2/1985 Seo
4,511,998 A 4/1985 Kanda et al.
4,539,847 A 9/1985 Paap
4,566,459 A 1/1986 Umemura et al.
4,567,768 A 2/1986 Satoh et al.
4,604,697 A 8/1986 Luthra et al.
4,662,222 A 5/1987 Johnson
4,669,482 A 6/1987 Ophir
4,682,497 A 7/1987 Sasaki
4,694,434 A 9/1987 Vonn Ramm et al.
4,781,199 A 11/1988 Hirama et al.
4,817,434 A 4/1989 Anderson
4,831,601 A 5/1989 Breimesser et al.
4,893,284 A 1/1990 Magrane
4,893,628 A 1/1990 Angelsen
4,990,462 A 2/1991 Sliwa, Jr.
5,027,658 A 7/1991 Anderson
5,050,588 A 9/1991 Grey et al.
5,060,205 A 10/1991 Phelan
5,062,295 A 11/1991 Shakkottai et al.
5,141,738 A 8/1992 Rasor et al.
5,161,536 A 11/1992 Vilkomerson et al.
5,197,475 A 3/1993 Antich et al.
5,226,019 A 7/1993 Bahorich
5,230,339 A 7/1993 Charlebois
5,269,309 A 12/1993 Fort et al.
5,278,757 A 1/1994 Hoctor et al.
5,293,871 A 3/1994 Reinstein et al.
5,299,576 A 4/1994 Shiba
5,301,674 A 4/1994 Erikson et al.
5,305,756 A 4/1994 Entrekin et al.
5,339,282 A 8/1994 Kuhn et al.
5,340,510 A 8/1994 Bowen
5,345,426 A 9/1994 Lipschutz
5,349,960 A 9/1994 Gondo
5,355,888 A 10/1994 Kendall
5,381,794 A 1/1995 Tel et al.
5,398,216 A 3/1995 Hall et al.
5,409,010 A 4/1995 Beach et al.
5,442,462 A 8/1995 Guissin
5,454,372 A 10/1995 Banjanin et al.
5,477,858 A 12/1995 Norris et al.
5,503,152 A 4/1996 Oakley et al.
5,515,853 A 5/1996 Smith et al.
5,515,856 A 5/1996 Olstad et al.
5,522,393 A 6/1996 Phillips et al.
5,526,815 A 6/1996 Granz et al.
5,544,659 A 8/1996 Banjanin
5,558,092 A 9/1996 Unger
5,564,423 A 10/1996 Mele et al.
5,568,812 A 10/1996 Murashita et al.
5,570,691 A 11/1996 Wright et al.
5,581,517 A 12/1996 Gee et al.
5,625,149 A 4/1997 Gururaja et al.
5,628,320 A 5/1997 Teo
5,666,953 A 9/1997 Wilk
5,673,697 A 10/1997 Bryan et al.
5,675,550 A 10/1997 Ekhaus
5,720,291 A 2/1998 Schwartz
5,720,708 A 2/1998 Lu et al.
5,744,898 A 4/1998 Smith et al.
5,769,079 A 6/1998 Hossack
5,784,334 A 7/1998 Sena et al.
5,785,654 A 7/1998 Iinuma et al.
5,795,297 A 8/1998 Daigle
5,797,845 A 8/1998 Barabash et al.
5,798,459 A 8/1998 Ohba et al.
5,817,023 A 10/1998 Daft
5,820,561 A 10/1998 Olstad et al.
5,838,564 A 11/1998 Bahorich et al.
5,850,622 A 12/1998 Vassiliou et al.
5,862,100 A 1/1999 VerWest
5,870,691 A 2/1999 Partyka et al.
5,871,446 A 2/1999 Wilk
5,876,342 A 3/1999 Chen et al.
5,891,038 A 4/1999 Seyed-Bolorforosh et al.
5,892,732 A 4/1999 Gersztenkorn
5,908,388 A 6/1999 Watkin et al.
5,916,169 A 6/1999 Hanafy et al.
5,919,139 A 7/1999 Lin
5,920,285 A 7/1999 Benjamin
5,930,730 A 7/1999 Marfurt et al.
5,938,612 A 8/1999 Kline-Schoder
5,940,778 A 8/1999 Marfurt et al.
5,951,479 A 9/1999 Holm et al.
5,964,707 A 10/1999 Fenster et al.
5,969,661 A 10/1999 Benjamin
5,999,836 A 12/1999 Nelson et al.
6,007,499 A 12/1999 Martin et al.
6,013,031 A 1/2000 Mendlein et al.
6,013,032 A 1/2000 Savord
6,014,473 A 1/2000 Hossack et al.
6,048,315 A 4/2000 Chiao et al.
6,049,509 A 4/2000 Sonneland et al.
6,050,943 A 4/2000 Slayton et al.
6,056,693 A 5/2000 Haider
6,058,074 A 5/2000 Swan et al.
6,077,224 A 6/2000 Lang et al.
6,092,026 A 7/2000 Bahorich et al.
6,122,538 A 9/2000 Sliwa, Jr. et al.
6,123,670 A 9/2000 Mo
6,129,672 A 10/2000 Seward et al.
6,135,960 A 10/2000 Holmberg
6,138,075 A 10/2000 Yost
6,148,095 A 11/2000 Prause et al.
6,162,175 A 12/2000 Marian, Jr. et al.
6,166,384 A 12/2000 Dentinger et al.
6,166,853 A 12/2000 Sapia et al.
6,190,318 B1 2/2001 Bab et al.
6,193,665 B1 2/2001 Hall et al.
6,196,739 B1 3/2001 Silverbrook
6,200,266 B1 3/2001 Shokrollahi et al.
6,210,335 B1 4/2001 Miller
6,213,958 B1 4/2001 Winder
6,221,019 B1 4/2001 Kantorovich
6,224,556 B1 5/2001 Schwartz et al.
6,231,511 B1 5/2001 Bae
6,238,342 B1 5/2001 Feleppa et al.
6,246,901 B1 6/2001 Benaron
6,251,073 B1 6/2001 Imran et al.
6,264,609 B1 7/2001 Herrington et al.
6,266,551 B1 7/2001 Osadchy et al.
6,278,949 B1 8/2001 Alam
6,279,399 B1 8/2001 Holm
6,289,230 B1 9/2001 Chaiken et al.

(56) References Cited

U.S. PATENT DOCUMENTS 6,299,580 B1 10/2001 Asafusa
6,304,684 B1 10/2001 Niczyporuk et al.
6,309,356 B1 10/2001 Ustuner et al.
6,324,453 B1 11/2001 Breed et al.
6,345,539 B1 2/2002 Rawes et al.
6,361,500 B1 3/2002 Masters
6,363,033 B1 3/2002 Cole et al.
6,370,480 B1 4/2002 Gupta et al.
6,373,984 B1 4/2002 Gouge et al.
6,374,185 B1 4/2002 Taner et al.
6,394,955 B1 5/2002 Perlitz
6,423,002 B1 7/2002 Hossack
6,431,175 B1 8/2002 Penner et al.
6,436,046 B1 8/2002 Napolitano et al.
6,449,821 B1 9/2002 Sudol et al.
6,450,965 B2 9/2002 Williams et al.
6,464,637 B1 10/2002 Criton et al.
6,468,216 B1 10/2002 Powers et al.
6,471,650 B2 10/2002 Powers et al.
6,475,150 B2 11/2002 Haddad
6,480,790 B1 11/2002 Calvert et al.
6,487,502 B1 11/2002 Taner
6,490,477 B1 12/2002 Zylka et al.
6,499,536 B1 12/2002 Ellingsen
6,503,204 B1 1/2003 Sumanaweera et al.
6,508,768 B1 1/2003 Hall et al.
6,508,770 B1 1/2003 Cai
6,514,205 B1 2/2003 Lee et al.
6,517,484 B1 2/2003 Wilk et al.
6,526,163 B1 2/2003 Halmann et al.
6,543,272 B1 4/2003 Vitek
6,547,732 B2 4/2003 Jago
6,551,246 B1 4/2003 Ustuner et al.
6,565,510 B1 5/2003 Haider
6,582,367 B1 6/2003 Robinson et al.
6,585,647 B1 7/2003 Winder
6,597,171 B2 7/2003 Hurlimann et al.
6,604,421 B1 8/2003 Li
6,614,560 B1 9/2003 Silverbrook
6,620,101 B2 9/2003 Azzam et al.
6,629,929 B1 10/2003 Jago et al.
6,645,147 B1 11/2003 Jackosn et al.
6,652,461 B1 11/2003 Levkovitz
6,668,654 B2 12/2003 Dubois et al.
6,672,165 B2 1/2004 Rather et al.
6,681,185 B1 1/2004 Young et al.
6,690,816 B2 2/2004 Aylward et al.
6,692,450 B1 2/2004 Coleman
6,695,778 B2 2/2004 Golland et al.
6,702,745 B1 3/2004 Smythe
6,704,692 B1 3/2004 Banerjee et al.
6,719,693 B2 4/2004 Richard
6,728,567 B2 4/2004 Rather et al.
6,752,762 B1 6/2004 DeJong et al.
6,755,787 B2 6/2004 Hossack et al.
6,780,152 B2 8/2004 Ustuner et al.
6,790,182 B2 9/2004 Eck et al.
6,835,178 B1 12/2004 Wilson et al.
6,837,853 B2 1/2005 Marian
6,843,770 B2 1/2005 Sumanaweera
6,847,737 B1 1/2005 Kouri et al.
6,854,332 B2 2/2005 Alleyne
6,865,140 B2 3/2005 Thomenius et al.
6,932,767 B2 8/2005 Landry et al.
7,033,320 B2 4/2006 Von Behren et al.
7,087,023 B2 8/2006 Daft et al.
7,104,956 B1 9/2006 Christopher
7,217,243 B2 5/2007 Takeuchi
7,221,867 B2 5/2007 Silverbrook
7,231,072 B2 6/2007 Yamano et al.
7,269,299 B2 9/2007 Schroeder
7,283,652 B2 10/2007 Mendonca et al.
7,285,094 B2 10/2007 Nohara et al.
7,293,462 B2 11/2007 Lee et al.
7,313,053 B2 12/2007 Wodnicki
7,366,704 B2 4/2008 Reading et al.
7,402,136 B2 7/2008 Hossack et al.
7,410,469 B1 8/2008 Talish et al.
7,415,880 B2 8/2008 Renzel
7,443,765 B2 10/2008 Thomenius et al.
7,444,875 B1 11/2008 Wu et al.
7,447,535 B2 11/2008 Lavi
7,448,998 B2 11/2008 Robinson
7,466,848 B2 12/2008 Metaxas et al.
7,469,096 B2 12/2008 Silverbrook
7,474,778 B2 1/2009 Shinomura et al.
7,481,577 B2 1/2009 Ramamurthy et al.
7,491,171 B2 2/2009 Barthe et al.
7,497,828 B1 3/2009 Wilk et al.
7,497,830 B2 3/2009 Li
7,510,529 B2 3/2009 Chou et al.
7,514,851 B2 4/2009 Wilser et al.
7,549,962 B2 6/2009 Dreschel et al.
7,574,026 B2 8/2009 Rasche et al.
7,625,343 B2 12/2009 Cao et al.
7,637,869 B2 12/2009 Sudol
7,668,583 B2 2/2010 Fegert et al.
7,674,228 B2 3/2010 Williams et al.
7,682,311 B2 3/2010 Simopoulos et al.
7,699,776 B2 4/2010 Walker et al.
7,722,541 B2 5/2010 Cai
7,744,532 B2 6/2010 Ustuner et al.
7,750,311 B2 7/2010 Daghighian
7,764,984 B2 7/2010 Desmedt et al.
7,785,260 B2 8/2010 Umemura et al.
7,787,680 B2 8/2010 Ahn et al.
7,806,828 B2 10/2010 Stringer
7,819,810 B2 10/2010 Stringer et al.
7,822,250 B2 10/2010 Yao et al.
7,824,337 B2 11/2010 Abe et al.
7,833,163 B2 11/2010 Cai
7,837,624 B1 11/2010 Hossack et al.
7,846,097 B2 12/2010 Jones et al.
7,850,613 B2 12/2010 Stribling
7,862,508 B2 1/2011 Davies et al.
7,876,945 B2 1/2011 Lötjönen
7,880,154 B2 2/2011 Otto
7,887,486 B2 2/2011 Ustuner et al.
7,901,358 B2 3/2011 Mehi et al.
7,914,451 B2 3/2011 Davies
7,919,906 B2 4/2011 Cerofolini
7,926,350 B2 4/2011 Kröning et al.
7,927,280 B2 4/2011 Davidsen
7,972,271 B2 7/2011 Johnson et al.
7,984,637 B2 7/2011 Ao et al.
7,984,651 B2 7/2011 Randall et al.
8,002,705 B1 8/2011 Napolitano et al.
8,007,439 B2 8/2011 Specht
8,057,392 B2 11/2011 Hossack et al.
8,057,393 B2 11/2011 Yao et al.
8,079,263 B2 12/2011 Randall et al.
8,079,956 B2 12/2011 Azuma et al.
8,088,067 B2 1/2012 Vortman et al.
8,088,068 B2 1/2012 Yao et al.
8,088,071 B2 1/2012 Hwang et al.
8,105,239 B2 1/2012 Specht
8,135,190 B2 3/2012 Bae et al.
8,157,737 B2 4/2012 Zhang et al.
8,182,427 B2 5/2012 Wu et al.
8,202,219 B2 6/2012 Luo et al.
8,265,175 B2 9/2012 Barsoum et al.
8,277,383 B2 10/2012 Specht
8,279,705 B2 10/2012 Choi et al.
8,343,054 B1 1/2013 Tamura
8,412,307 B2 4/2013 Willis et al.
8,414,564 B2 4/2013 Goldshleger et al.
8,419,642 B2 4/2013 Sandrin et al.
8,473,239 B2 6/2013 Specht et al.
8,478,382 B2 7/2013 Burnside et al.
8,483,804 B2 7/2013 Hsieh et al.
8,532,951 B2 9/2013 Roy et al.
8,539,838 B2 9/2013 Yoo et al.
8,582,848 B2 11/2013 Funka-Lea et al.
8,602,993 B2 12/2013 Specht et al.

(56) References Cited

U.S. PATENT DOCUMENTS 8,627,724 B2 1/2014 Papadopoulos et al.
8,634,615 B2 1/2014 Brabec
8,672,846 B2 3/2014 Napolitano et al.
8,684,936 B2 4/2014 Specht
9,036,887 B2 5/2015 Fouras et al.
9,072,495 B2 7/2015 Specht
9,146,313 B2 9/2015 Specht et al.
9,152,761 B2 10/2015 Bhatia et al.
9,176,078 B2 11/2015 Flohr et al.
9,192,355 B2 11/2015 Specht et al.
9,217,660 B2 12/2015 Zlotnick et al.
9,220,478 B2 12/2015 Smith et al.
9,247,874 B2 2/2016 Kumar et al.
9,247,926 B2 2/2016 Smith et al.
9,265,484 B2 2/2016 Brewer et al.
9,268,777 B2 2/2016 Lu et al.
9,271,661 B2 3/2016 Moghari et al.
9,277,861 B2 3/2016 Kowal et al.
9,282,945 B2 3/2016 Smith et al.
9,339,239 B2 5/2016 Wang et al.
9,339,256 B2 5/2016 Specht et al.
9,392,986 B2 7/2016 Ning et al.
9,420,994 B2 8/2016 Specht
9,510,806 B2 12/2016 Smith et al.
9,526,475 B2 12/2016 Specht et al.
9,526,485 B2 12/2016 Yang
9,572,549 B2 2/2017 Belevich et al.
9,576,354 B2 2/2017 Fouras et al.
9,582,876 B2 2/2017 Specht
9,606,206 B2 3/2017 Boernert et al.
9,659,152 B2 5/2017 Mueller
9,668,714 B2 6/2017 Call et al.
9,706,972 B1 7/2017 Ahn et al.
9,775,511 B2 10/2017 Kumar et al.
9,788,813 B2 10/2017 Adam et al.
9,883,848 B2 * 2/2018 Specht ................ G01S 15/8915
9,901,407 B2 2/2018 Breisacher et al.
9,986,969 B2 6/2018 Call et al.
9,986,975 B2 6/2018 Specht et al.
10,064,605 B2 9/2018 Belevich et al.
10,130,333 B2 11/2018 Specht
10,206,662 B2 2/2019 Smith et al.
10,226,234 B2 3/2019 Specht et al.
10,267,913 B2 4/2019 Smith et al.
10,342,518 B2 7/2019 Specht et al.
10,380,399 B2 8/2019 Call et al.
10,401,493 B2 9/2019 Call et al.
10,586,846 B2 3/2020 Bolotnikov et al.
10,617,384 B2 4/2020 Brewer et al.
10,653,392 B2 5/2020 Specht et al.
10,675,000 B2 6/2020 Specht et al.
10,695,027 B2 6/2020 Call et al.
10,835,208 B2 11/2020 Smith et al.
10,854,846 B2 12/2020 Kim et al.
10,856,846 B2 12/2020 Davis et al.
10,925,577 B2 2/2021 Adam et al.
11,016,191 B2 5/2021 Call et al.
11,051,791 B2 7/2021 Smith et al.
11,068,689 B2 7/2021 Call et al.
11,096,662 B2 8/2021 Specht
11,172,911 B2 11/2021 Call et al.
11,253,233 B2 2/2022 Belevich et al.
11,464,492 B2 10/2022 Specht et al.
11,678,861 B2 6/2023 Call et al.
11,709,265 B2 7/2023 Call et al.
11,723,626 B2 8/2023 Smith et al.
12,426,855 B2 * 9/2025 Specht ................ A61B 8/4483
2002/0035864 A1 3/2002 Paltieli et al.
2002/0073781 A1 6/2002 Hashimoto et al.
2002/0087071 A1 7/2002 Schmitz et al.
2002/0111568 A1 8/2002 Bukshpan
2002/0138003 A1 9/2002 Bukshpan
2002/0161299 A1 10/2002 Prater et al.
2003/0007598 A1 1/2003 Wang et al.
2003/0013962 A1 1/2003 Bjaerum et al.
2003/0028111 A1 2/2003 Vaezy et al.
2003/0040669 A1 2/2003 Grass et al.
2003/0163271 A1 8/2003 Chell et al.
2003/0181806 A1 9/2003 Medan et al.
2003/0220554 A1 11/2003 Grenon et al.
2003/0228053 A1 12/2003 Li et al.
2004/0015079 A1 1/2004 Berger et al.
2004/0054283 A1 3/2004 Corey et al.
2004/0068184 A1 4/2004 Trahey et al.
2004/0100163 A1 5/2004 Baumgartner et al.
2004/0111028 A1 6/2004 Abe et al.
2004/0122313 A1 6/2004 Moore et al.
2004/0122322 A1 6/2004 Moore et al.
2004/0127793 A1 7/2004 Mendlein et al.
2004/0138565 A1 7/2004 Trucco
2004/0144176 A1 7/2004 Yoden
2004/0215075 A1 10/2004 Zagzebski et al.
2004/0236217 A1 11/2004 Cerwin et al.
2004/0236223 A1 11/2004 Barnes et al.
2004/0258127 A1 12/2004 Ramamurthy et al.
2004/0267132 A1 12/2004 Podany
2005/0004449 A1 1/2005 Mitschke et al.
2005/0053305 A1 3/2005 Li et al.
2005/0054910 A1 3/2005 Tremblay et al.
2005/0061536 A1 3/2005 Proulx
2005/0090743 A1 4/2005 Kawashima et al.
2005/0090745 A1 4/2005 Steen
2005/0111846 A1 5/2005 Steinbacher et al.
2005/0113689 A1 5/2005 Gritzky
2005/0113694 A1 5/2005 Haugen et al.
2005/0124883 A1 6/2005 Hunt
2005/0131300 A1 6/2005 Bakircioglu et al.
2005/0147297 A1 7/2005 McLaughlin et al.
2005/0148874 A1 7/2005 Brock-Fisher et al.
2005/0165312 A1 7/2005 Knowles et al.
2005/0197573 A1 9/2005 Roth et al.
2005/0203404 A1 9/2005 Freiburger
2005/0215883 A1 9/2005 Hundley et al.
2005/0240125 A1 10/2005 Makin et al.
2005/0251013 A1 11/2005 Krishan et al.
2005/0252295 A1 11/2005 Fink et al.
2005/0281447 A1 12/2005 Moreau-Gobard et al.
2005/0288588 A1 12/2005 Weber et al.
2006/0036170 A1 2/2006 Lachaine et al.
2006/0058664 A1 3/2006 Barthe et al.
2006/0062447 A1 3/2006 Rinck et al.
2006/0074313 A1 4/2006 Slayton et al.
2006/0074315 A1 4/2006 Liang et al.
2006/0074320 A1 4/2006 Yoo et al.
2006/0079759 A1 4/2006 Vaillant et al.
2006/0079778 A1 4/2006 Mo et al.
2006/0079782 A1 4/2006 Beach et al.
2006/0094962 A1 5/2006 Clark
2006/0111634 A1 5/2006 Wu
2006/0122506 A1 6/2006 Davies et al.
2006/0173327 A1 8/2006 Kim
2006/0256231 A1 11/2006 Sasaki et al.
2006/0262961 A1 11/2006 Holsing et al.
2006/0270934 A1 11/2006 Savord et al.
2007/0016022 A1 1/2007 Blalock et al.
2007/0016044 A1 1/2007 Blalock et al.
2007/0036414 A1 2/2007 Georgescu et al.
2007/0043290 A1 2/2007 Goepp et al.
2007/0055155 A1 3/2007 Owen et al.
2007/0073781 A1 3/2007 Adkins et al.
2007/0078345 A1 4/2007 Mo et al.
2007/0083109 A1 4/2007 Ustuner et al.
2007/0088213 A1 4/2007 Poland
2007/0138157 A1 6/2007 Dane et al.
2007/0161898 A1 7/2007 Hao et al.
2007/0161904 A1 7/2007 Urbano
2007/0167752 A1 7/2007 Proulx et al.
2007/0167824 A1 7/2007 Lee et al.
2007/0232914 A1 10/2007 Chen et al.
2007/0238985 A1 10/2007 Smith et al.
2007/0242567 A1 10/2007 Daft et al.
2008/0009739 A1 1/2008 Chiang et al.
2008/0044572 A1 2/2008 Loeffler et al.
2008/0110261 A1 5/2008 Randall et al.

(56) References Cited

U.S. PATENT DOCUMENTS

2008/0110263 A1 5/2008 Klessel et al.
2008/0112265 A1 5/2008 Urbano et al.
2008/0114241 A1 5/2008 Randall et al.
2008/0114245 A1 5/2008 Randall et al.
2008/0114246 A1 5/2008 Randall et al.
2008/0114247 A1 5/2008 Urbano et al.
2008/0114248 A1 5/2008 Urbano et al.
2008/0114249 A1 5/2008 Randall et al.
2008/0114250 A1 5/2008 Urbano et al.
2008/0114251 A1 5/2008 Weymer et al.
2008/0114252 A1 5/2008 Randall et al.
2008/0114253 A1 5/2008 Randall et al.
2008/0114255 A1 5/2008 Schwartz et al.
2008/0125659 A1 5/2008 Wilser et al.
2008/0132790 A1 6/2008 Burton
2008/0181479 A1 7/2008 Yang et al.
2008/0183075 A1 7/2008 Govari et al.
2008/0188747 A1 8/2008 Randall et al.
2008/0188750 A1 8/2008 Randall et al.
2008/0194957 A1 8/2008 Hoctor et al.
2008/0194958 A1 8/2008 Lee et al.
2008/0194959 A1 8/2008 Wang et al.
2008/0208061 A1 8/2008 Halmann
2008/0242996 A1 10/2008 Hall et al.
2008/0249408 A1 10/2008 Palmeri et al.
2008/0255452 A1 10/2008 Entrekin
2008/0262357 A1 10/2008 Wodnicki
2008/0269604 A1 10/2008 Boctor et al.
2008/0269613 A1 10/2008 Summers et al.
2008/0275344 A1 11/2008 Glide-Hurst et al.
2008/0285819 A1 11/2008 Konofagou et al.
2008/0287787 A1 11/2008 Sauer et al.
2008/0294045 A1 11/2008 Ellington et al.
2008/0294050 A1 11/2008 Shinomura et al.
2008/0294052 A1 11/2008 Wilser et al.
2008/0306382 A1 12/2008 Guracar et al.
2008/0306386 A1 12/2008 Baba et al.
2008/0319317 A1 12/2008 Kamiyama et al.
2008/0319318 A1 12/2008 Johnson et al.
2009/0005679 A1 1/2009 Dala-Krishna
2009/0010459 A1 1/2009 Garbini et al.
2009/0012393 A1 1/2009 Choi
2009/0015665 A1 1/2009 Willsie
2009/0016163 A1 1/2009 Freeman et al.
2009/0018445 A1 1/2009 Schers et al.
2009/0024039 A1 1/2009 Wang et al.
2009/0036780 A1 2/2009 Abraham
2009/0043206 A1 2/2009 Towfiq et al.
2009/0048519 A1 2/2009 Hossack et al.
2009/0069681 A1 3/2009 Lundberg et al.
2009/0069686 A1 3/2009 Daft et al.
2009/0069692 A1 3/2009 Cooley et al.
2009/0079299 A1 3/2009 Bradley et al.
2009/0099483 A1 4/2009 Rybyanets
2009/0112095 A1 4/2009 Daigle
2009/0131797 A1 5/2009 Jeong et al.
2009/0143680 A1 6/2009 Yao et al.
2009/0148012 A1 6/2009 Altmann et al.
2009/0150094 A1 6/2009 Van Velsor et al.
2009/0182233 A1 7/2009 Wodnicki
2009/0182237 A1 7/2009 Angelsen et al.
2009/0198134 A1 8/2009 Hashimoto et al.
2009/0203997 A1 8/2009 Ustuner
2009/0208080 A1 8/2009 Grau et al.
2009/0259128 A1 10/2009 Stribling
2009/0264760 A1 10/2009 Lazebnik et al.
2009/0306510 A1 12/2009 Hashiba et al.
2009/0326379 A1 12/2009 Daigle et al.
2010/0010354 A1 1/2010 Skerl et al.
2010/0016725 A1 1/2010 Thiele
2010/0036258 A1 2/2010 Dietz et al.
2010/0063397 A1 3/2010 Wagner
2010/0063399 A1 3/2010 Walker et al.
2010/0069751 A1 3/2010 Hazard et al.
2010/0069756 A1 3/2010 Ogasawara et al.
2010/0085383 A1 4/2010 Cohen et al.
2010/0106431 A1 4/2010 Baba et al.
2010/0109481 A1 5/2010 Buccafusca
2010/0121193 A1 5/2010 Fukukita et al.
2010/0121196 A1 5/2010 Hwang et al.
2010/0130855 A1 5/2010 Lundberg et al.
2010/0145195 A1 6/2010 Hyun
2010/0168566 A1 7/2010 Bercoff et al.
2010/0168578 A1 7/2010 Garson, Jr. et al.
2010/0174194 A1 7/2010 Chiang et al.
2010/0174198 A1 7/2010 Young et al.
2010/0191110 A1 7/2010 Insana et al.
2010/0217124 A1 8/2010 Cooley
2010/0217125 A1 8/2010 Kadokura et al.
2010/0228126 A1 9/2010 Emery et al.
2010/0240994 A1 9/2010 Zheng
2010/0249596 A1 9/2010 Magee
2010/0256488 A1 10/2010 Kim et al.
2010/0262013 A1 10/2010 Smith et al.
2010/0266176 A1 10/2010 Masumoto et al.
2010/0286525 A1 11/2010 Osumi
2010/0286527 A1 11/2010 Cannon et al.
2010/0298712 A1 11/2010 Pelissier et al.
2010/0310143 A1 12/2010 Rao et al.
2010/0317971 A1 12/2010 Fan et al.
2010/0324418 A1 12/2010 El-Aklouk et al.
2010/0324423 A1 12/2010 El-Aklouk et al.
2010/0329521 A1 12/2010 Beymer et al.
2011/0005322 A1 1/2011 Ustuner
2011/0016977 A1 1/2011 Guracar
2011/0021920 A1 1/2011 Shafir et al.
2011/0021923 A1 1/2011 Daft et al.
2011/0033098 A1 2/2011 Richter et al.
2011/0044133 A1 2/2011 Tokita
2011/0066030 A1 3/2011 Yao
2011/0098565 A1 4/2011 Masuzawa
2011/0112400 A1 5/2011 Emery et al.
2011/0112404 A1 5/2011 Gourevitch
2011/0125017 A1 5/2011 Ramamurthy et al.
2011/0178441 A1 7/2011 Tyler
2011/0196237 A1 8/2011 Pelissier et al.
2011/0213244 A1 9/2011 Frinking et al.
2011/0270088 A1 11/2011 Shiina
2011/0301470 A1 12/2011 Sato et al.
2011/0306886 A1 12/2011 Daft et al.
2011/0319764 A1 12/2011 Okada et al.
2012/0004545 A1 1/2012 Ziv-Ari et al.
2012/0035482 A1 2/2012 Kim et al.
2012/0036934 A1 2/2012 Kröning et al.
2012/0071710 A1 3/2012 Gazdzinski
2012/0085173 A1 4/2012 Papadopoulos et al.
2012/0101378 A1 4/2012 Lee
2012/0114210 A1 5/2012 Kim et al.
2012/0121150 A1 5/2012 Murashita
2012/0137778 A1 6/2012 Kitazawa et al.
2012/0140595 A1 6/2012 Amemiya
2012/0141002 A1 6/2012 Urbano et al.
2012/0165670 A1 6/2012 Shi et al.
2012/0179044 A1 7/2012 Chiang et al.
2012/0209150 A1 8/2012 Zeng et al.
2012/0226201 A1 9/2012 Clark et al.
2012/0235998 A1 9/2012 Smith-Casem et al.
2012/0243763 A1 9/2012 Wen et al.
2012/0253194 A1 10/2012 Tamura
2012/0265075 A1 10/2012 Pedrizzetti et al.
2012/0277585 A1 11/2012 Koenig et al.
2012/0283564 A1 11/2012 Ebbini et al.
2013/0030296 A1 1/2013 Miyaki
2013/0046168 A1 2/2013 Sui
2013/0070062 A1 3/2013 Fouras et al.
2013/0076207 A1 3/2013 Krohn et al.
2013/0079639 A1 3/2013 Hoctor et al.
2013/0083628 A1 4/2013 Qiao et al.
2013/0088122 A1 4/2013 Krohn et al.
2013/0116561 A1 5/2013 Rothberg et al.
2013/0128702 A1 5/2013 Degertekin et al.
2013/0131516 A1 5/2013 Katsuyama
2013/0144165 A1 6/2013 Ebbini et al.
2013/0204136 A1 8/2013 Duric et al.

(56) References Cited

U.S. PATENT DOCUMENTS

| | | | |
|---|---|---|---|
| 2013/0204137 A1 | 8/2013 | Roy et al. | |
| 2013/0237799 A1 | 9/2013 | Motoki | |
| 2013/0258805 A1 | 10/2013 | Hansen et al. | |
| 2013/0261463 A1 | 10/2013 | Chiang et al. | |
| 2013/0310688 A1 | 11/2013 | Rosen et al. | |
| 2013/0317331 A1 | 11/2013 | Bechtel et al. | |
| 2013/0338474 A9 | 12/2013 | Carson et al. | |
| 2013/0345566 A1 | 12/2013 | Weitzel et al. | |
| 2014/0056099 A1 | 2/2014 | Hancock | |
| 2014/0073921 A1 | 3/2014 | Specht et al. | |
| 2014/0086014 A1 | 3/2014 | Kobayashi | |
| 2014/0147013 A1 | 5/2014 | Shandas et al. | |
| 2014/0243673 A1 | 8/2014 | Anand et al. | |
| 2015/0045668 A1 | 2/2015 | Smith et al. | |
| 2015/0080727 A1* | 3/2015 | Specht | G01S 15/8915 600/443 |
| 2015/0172878 A1 | 6/2015 | Luna et al. | |
| 2015/0224346 A1 | 8/2015 | Coviello et al. | |
| 2016/0093024 A1 | 3/2016 | Kang et al. | |
| 2016/0223632 A1 | 8/2016 | Baek et al. | |
| 2016/0228090 A1 | 8/2016 | Boctor et al. | |
| 2017/0119352 A1 | 5/2017 | Anand et al. | |
| 2017/0363725 A1 | 12/2017 | Ignjatovic et al. | |
| 2018/0116631 A1 | 5/2018 | Taniguchi | |
| 2018/0125451 A1 | 5/2018 | Duncan et al. | |
| 2018/0153511 A1 | 6/2018 | Specht et al. | |
| 2019/0082117 A1 | 3/2019 | Moore et al. | |
| 2019/0200961 A1 | 7/2019 | Specht et al. | |
| 2019/0211175 A1 | 7/2019 | Wang et al. | |
| 2019/0251724 A1 | 8/2019 | Schreckenberg et al. | |
| 2019/0261949 A1 | 8/2019 | Labyed | |
| 2019/0261956 A1 | 8/2019 | Srinivasan | |
| 2019/0380677 A1 | 12/2019 | Ono et al. | |
| 2020/0069292 A1 | 3/2020 | Abolmaesumi et al. | |
| 2020/0275910 A1 | 9/2020 | Specht et al. | |
| 2020/0297320 A1 | 9/2020 | Specht et al. | |
| 2021/0085292 A1 | 3/2021 | Davis et al. | |
| 2021/0350101 A1 | 11/2021 | Call et al. | |
| 2021/0378633 A1 | 12/2021 | Specht et al. | |
| 2022/0071601 A1 | 3/2022 | Call et al. | |
| 2022/0167949 A1 | 6/2022 | Belevich et al. | |
| 2023/0248333 A1* | 8/2023 | Bajikar | G01S 15/8929 |
| 2023/0277158 A1 | 9/2023 | Brewer et al. | |
| 2024/0041436 A1 | 2/2024 | Wang et al. | |
| 2024/0081787 A1 | 3/2024 | Specht et al. | |
| 2025/0176948 A1 | 6/2025 | Belevich et al. | |

FOREIGN PATENT DOCUMENTS

| | | | |
|---|---|---|---|
| CN | 1781460 | A | 6/2006 |
| CN | 101103927 | A | 1/2008 |
| CN | 101116622 | A | 2/2008 |
| CN | 101190134 | A | 6/2008 |
| CN | 101453955 | A | 6/2009 |
| CN | 100545650 | C | 9/2009 |
| CN | 101609150 | A | 12/2009 |
| CN | 101852773 | A | 6/2010 |
| CN | 101785684 | A | 7/2010 |
| CN | 101843501 | A | 9/2010 |
| CN | 101912278 | A | 12/2010 |
| CN | 101965232 | A | 2/2011 |
| CN | 102018533 | A | 4/2011 |
| CN | 102112047 | A | 6/2011 |
| CN | 102123668 | A | 7/2011 |
| CN | 102258388 | A | 11/2011 |
| CN | 102283679 | A | 12/2011 |
| CN | 102599930 | A | 7/2012 |
| CN | 103792288 | A | 5/2014 |
| CN | 104080407 | A | 10/2014 |
| CN | 104105449 | A | 10/2014 |
| CN | 104620128 | A | 5/2015 |
| DE | 102011114333 | A1 | 3/2013 |
| EP | 1346689 | A2 | 9/2003 |
| EP | 1944070 | A1 | 7/2008 |
| EP | 1949856 | A1 | 7/2008 |
| EP | 2058796 | A2 | 5/2009 |
| EP | 2101191 | A2 | 9/2009 |
| EP | 2182352 | A2 | 5/2010 |
| EP | 2187813 | A1 | 5/2010 |
| EP | 2198785 | A1 | 6/2010 |
| EP | 1757955 | B1 | 11/2010 |
| EP | 2319417 | A1 | 5/2011 |
| EP | 2325672 | A1 | 5/2011 |
| EP | 1462819 | B1 | 7/2011 |
| EP | 2356941 | A1 | 8/2011 |
| EP | 1979739 | B1 | 10/2011 |
| EP | 2385391 | A2 | 11/2011 |
| EP | 2294400 | B1 | 2/2012 |
| EP | 2453256 | A2 | 5/2012 |
| EP | 1840594 | B1 | 6/2012 |
| EP | 2514368 | A1 | 10/2012 |
| EP | 1850743 | B1 | 12/2012 |
| EP | 1594404 | B1 | 9/2013 |
| EP | 2026280 | B1 | 10/2013 |
| FR | 2851662 | A1 | 8/2004 |
| JP | 49-11189 | A | 1/1974 |
| JP | 54-44375 | A | 4/1979 |
| JP | 55-103839 | A | 8/1980 |
| JP | 57-31848 | A | 2/1982 |
| JP | 58-223059 | A | 12/1983 |
| JP | 59-101143 | A | 6/1984 |
| JP | 59-174151 | A | 10/1984 |
| JP | 60-13109 | U | 1/1985 |
| JP | 60-68836 | A | 4/1985 |
| JP | 01164354 | A | 6/1989 |
| JP | 02501431 | A | 5/1990 |
| JP | 03015455 | A | 1/1991 |
| JP | 03126443 | A | 5/1991 |
| JP | 04017842 | A | 1/1992 |
| JP | 04067856 | A | 3/1992 |
| JP | 05042138 | A | 2/1993 |
| JP | H05146437 | A | 6/1993 |
| JP | 06125908 | A | 5/1994 |
| JP | 06254092 | A | 9/1994 |
| JP | 07051266 | A | 2/1995 |
| JP | 07204201 | A | 8/1995 |
| JP | H07204202 | A | 8/1995 |
| JP | 08154930 | A | 6/1996 |
| JP | 08252253 | A | 10/1996 |
| JP | H0315455 | A | 1/1997 |
| JP | 09103429 | A | 4/1997 |
| JP | 09201361 | A | 8/1997 |
| JP | 2777197 | B | 5/1998 |
| JP | 10216128 | A | 8/1998 |
| JP | 11089833 | A | 4/1999 |
| JP | 11239578 | A | 9/1999 |
| JP | 2001507794 | A | 6/2001 |
| JP | 2001245884 | A | 9/2001 |
| JP | 2002209894 | A | 7/2002 |
| JP | 2002253548 | A | 9/2002 |
| JP | 2002253549 | A | 9/2002 |
| JP | 2003235839 | A | 8/2003 |
| JP | 2003290224 | A | 10/2003 |
| JP | 2004167092 | A | 6/2004 |
| JP | 2004215987 | A | 8/2004 |
| JP | 2004337457 | A | 12/2004 |
| JP | 2004340809 | A | 12/2004 |
| JP | 2004351214 | A | 12/2004 |
| JP | 2005046192 | A | 2/2005 |
| JP | 2005046193 | A | 2/2005 |
| JP | 2005152187 | A | 6/2005 |
| JP | 2005523792 | A | 8/2005 |
| JP | 2005526539 | A | 9/2005 |
| JP | 2006051356 | A | 2/2006 |
| JP | 2006061203 | A | 3/2006 |
| JP | 2006122657 | A | 5/2006 |
| JP | 2006130313 | A | 5/2006 |
| JP | 2006204923 | A | 8/2006 |
| JP | 2007325937 | A | 12/2007 |
| JP | 2008122209 | A | 5/2008 |
| JP | 2008513763 | A | 5/2008 |
| JP | 2008515557 | A | 5/2008 |
| JP | 2008132342 | A | 6/2008 |

(56) References Cited

FOREIGN PATENT DOCUMENTS

| | | | |
|---|---|---|---|
| JP | 2008522642 | A | 7/2008 |
| JP | 2008259541 | A | 10/2008 |
| JP | 2008279274 | A | 11/2008 |
| JP | 2008307087 | A | 12/2008 |
| JP | 2009178448 | A | 8/2009 |
| JP | 2009240667 | A | 10/2009 |
| JP | 2010005375 | A | 1/2010 |
| JP | 2010124842 | A | 6/2010 |
| JP | 2010526626 | A | 8/2010 |
| JP | 2010227487 | A | 10/2010 |
| JP | 2010227503 | A | 10/2010 |
| JP | 2011527586 | A | 11/2011 |
| JP | 2011529362 | A | 12/2011 |
| JP | 2013118984 | A | 6/2013 |
| JP | 2013121493 | A | 6/2013 |
| JP | 2015532607 | A | 2/2014 |
| JP | 2014087448 | A | 5/2014 |
| JP | 2015500062 | A | 1/2015 |
| JP | 2018068852 | A | 5/2018 |
| JP | 2018512943 | A | 5/2018 |
| JP | 2018118081 | A | 8/2018 |
| JP | 2019111104 | A | 7/2019 |
| JP | 2020014857 | A | 1/2020 |
| KR | 100715132 | B | 4/2007 |
| KR | 1020080044737 | A | 5/2008 |
| KR | 1020090009258 | A | 1/2009 |
| KR | 1020090103408 | A | 10/2009 |
| KR | 1020100051108 | A | 5/2010 |
| KR | 1020130060875 | A | 6/2013 |
| KR | 1020130089645 | A | 8/2013 |
| KR | 1020140034114 | A | 3/2014 |
| KR | 1020140069664 | A | 6/2014 |
| KR | 1020140098843 | A | 8/2014 |
| KR | 102176193 | B1 | 4/2015 |
| WO | WO92/18054 | A1 | 10/1992 |
| WO | WO98/00719 | A2 | 1/1998 |
| WO | WO01/64109 | A1 | 9/2001 |
| WO | WO02/17296 | A1 | 2/2002 |
| WO | WO02/084594 | A2 | 10/2002 |
| WO | WO2005/009245 | A1 | 2/2005 |
| WO | WO2006/113445 | A1 | 10/2006 |
| WO | WO2006/114735 | A1 | 11/2006 |
| WO | WO2007/013814 | A2 | 2/2007 |
| WO | WO2007/127147 | A2 | 11/2007 |
| WO | WO2008/097479 | A1 | 8/2008 |
| WO | WO2008/127927 | A1 | 10/2008 |
| WO | WO2008/137030 | A1 | 11/2008 |
| WO | WO2009/060182 | A2 | 5/2009 |
| WO | WO2010/095094 | A1 | 8/2010 |
| WO | WO2010/137453 | A1 | 12/2010 |
| WO | WO2010/139519 | A1 | 12/2010 |
| WO | WO2011/004661 | A1 | 1/2011 |
| WO | WO2011/057252 | A1 | 5/2011 |
| WO | WO2011/064688 | A1 | 6/2011 |
| WO | WO2011/094585 | A | 8/2011 |
| WO | WO2011/100697 | A1 | 8/2011 |
| WO | WO2011/123529 | A1 | 10/2011 |
| WO | WO2012/028896 | A1 | 3/2012 |
| WO | WO2012/033093 | A1 | 3/2012 |
| WO | WO2012/049124 | A2 | 4/2012 |
| WO | WO2012/049612 | A2 | 4/2012 |
| WO | WO2012/078639 | A1 | 6/2012 |
| WO | WO2012/091280 | A1 | 7/2012 |
| WO | WO2012/112540 | A2 | 8/2012 |
| WO | WO2012/131340 | A2 | 10/2012 |
| WO | WO2012/160541 | A2 | 11/2012 |
| WO | WO2013/030556 | A1 | 3/2013 |
| WO | WO2013/059358 | A2 | 4/2013 |
| WO | WO2013/109965 | A1 | 7/2013 |
| WO | WO2013/116807 | A1 | 8/2013 |
| WO | WO2013/116809 | A1 | 8/2013 |
| WO | WO2013/116851 | A1 | 8/2013 |
| WO | WO2013/116854 | A1 | 8/2013 |
| WO | WO2013/116866 | A1 | 8/2013 |
| WO | WO2013/126559 | A1 | 8/2013 |
| WO | WO2013/128301 | A2 | 9/2013 |
| WO | WO2016/093024 | A1 | 6/2016 |
| WO | WO2019/211175 | A1 | 11/2019 |
| WO | WO2022/086521 | A1 | 4/2022 |
| WO | WO2022/094465 | A1 | 5/2022 |
| WO | WO2023/049529 | A1 | 3/2023 |

OTHER PUBLICATIONS

Specht et al.; U.S. Appl. No. 18/588,967 entitled "Determining material stiffness using multiple aperaure ultrasound," filed Feb. 27, 2024.

Jensen et al.; Synthetic aperture ultrasound imaging; Ultrasonics; vol. 44; pp. e5-e15; Dec. 22, 2006.

Call et al.; U.S. Appl. No. 18/330,699 entitled "Network-based ultrasound imaging system," filed Jun. 7, 2023.

Atmeh et al.; U.S. Appl. No. 18/251,421 entitled "Systems and methods for improving ultrasound image quality," filed May 2, 2023.

Smith et al.; U.S. Appl. No. 18/344,278 entitled "Concave ultrasound transducers and 3d arrays," filed Jun. 29, 2023.

Call et al.; U.S. Appl. No. 18/344,479 entitled "Ultrasound imaging systems and methods for detecting object motion," filed Jun. 29, 2023.

Narayan et al.; Speckle in ultrasound images: Friend or FOE?; In 2014 IEEE International Conference on Image Processing (ICIP); pp. 5816-5820; Oct. 27, 2014.

Davis et al.; U.S. Appl. No. 18/763,696 entitled "Ultrasound imaging with sparse array probes," filed Jul. 3, 2024.

Specht et al.; U.S. Appl. No. 18/646,623 entitled "Point source transmission and speed-of-sound correctionusing multi-aperture ultrasound imaging," filed Apr. 25, 2024.

Abeysekera et al.; Alignment and calibration of dual ultrasound transducers using a wedge phantom; Ultrasound in Medicine and Biology; 37(2); pp. 271-279; Feb. 2011.

Arigovindan et al.; Full motion and flow field recovery from echo doppler data; IEEE Transactions on Medical Imaging; 26(1); pp. 31-45; Jan. 2007.

Capineri et al.; A doppler system for dynamic vector velocity maps; Ultrasound in Medicine & Biology; 28(2); pp. 237-248; Feb. 28, 2002.

Carson et al.; Measurement of photoacoustic transducer position by robotic source placement and nonlinear parameter estimation; Biomedical Optics (BiOS): International Society for Optics and Photonics (9th Conf. on Biomedical Thermoacoustics, Optoacoustics, and Acousto-optics; vol. 6856; 9 pages; Feb. 28, 2008.

Chen et al.; Maximum-likelihood source localization and unknown sensor location estimation for wideband signals in the near-field; IEEE Transactions On Signal Processing; 50(8); pp. 1843-1854; Aug. 2002.

Chen et al.; Source localization and tracking of a wideband source using a randomly distributed beamforming sensor array; International Journal of High Performance Computing Applications; 16(3); pp. 259-272; Fall 2002.

Cristianini et al.; An Introduction to Support Vector Machines; Cambridge University Press; pp. 93-111; Mar. 2000.

Dunmire et al.; A brief history of vector doppler; Medical Imaging 2001; International Society for Optics and Photonics; pp. 200-214; May 30, 2001.

Dunmire et al.; Cross-beam vector Doppler ultrasound for angle-independent velocity measurements; Ultrasound in medicine & biology; 26(8); pp. 1213-1235; Oct. 2000.

Du et al.; User parameter free approaches to multistatic adaptive ultrasound imaging; 5th IEEE International Symposium; pp. 1287-1290, May 2008.

Feigenbaum, Harvey, M.D.; Echocardiography; Lippincott Williams & Wilkins; Philadelphia; 5th Ed.; pp. 482, 484; Feb. 1994.

Fernandez et al.; High resolution ultrasound beamforming using synthetic and adaptive imaging techniques; Proceedings IEEE International Symposium on Biomedical Imaging; Washington, D.C.; pp. 433-436; Jul. 7-10, 2002.

(56) References Cited

OTHER PUBLICATIONS

Gazor et al.; Wideband multi-source beamforming with array location calibration and direction finding: Conference on Acoustics, Speech and Signal Processing ICASSP-95; Detroit, MI; vol. 3 IEEE; pp. 1904-1907; May 9-12, 1995.
Gran et al.; Directional velocity estimation using a spatio-temporal encoding technique based on frequency division for synthetic transmit aperture ultrasound; IEEE transactions on ultrasonics, ferroelectrics, and frequency control; 53(7); pp. 1289-1299; Aug. 2006.
Haykin, Simon; Neural Networks: A Comprehensive Foundation (2nd Ed.); Prentice Hall; pp. 156-187; Jul. 16, 1998.
Heikkila et al.; A four-step camera calibration procedure with implicit image correction; Proceedings IEEE Computer Scociety Conference on Computer Vision and Pattern Recognition, San Juan; pp. 1106-1112; Jun. 17-19, 1997.
Hendee et al.; Medical Imaging Physics; Wiley-Liss, Inc. 4th Edition; Chap. 19-22; pp. 303-353; © 2002 (the year of publication is sufficiently earlier than the effective U.S. filing date and any foreign priority date so that the particular month of publication is not in issue).
Holzner; How to Find Vector Components; 5 pages; retrieved from the internet (https://www.dummies.com/education/science/physics/how-to-find-vector-components/); Mar. 2021.
Hsu et al.; Real-time freehand 3D ultrasound calibration; CUED/F-INFENG/TR 565; Department of Engineering, University of Cambridge, United Kingdom; 14 pages; Sep. 2006.
Jeffs; Beamforming: a brief introduction; Brigham Young University; 14 pages; retrieved from the internet (http://ens.ewi.tudelft.nl/Education/courses/et4235/Beamforming.pdf); Oct. 2004.
Khamene et al.; A novel phantom-less spatial and temporal ultrasound calibration method; Medical Image Computing and Computer-Assisted Intervention—MICCAI (Proceedings 8th Int. Conf.); Springer Berlin Heidelberg; Palm Springs, CA; pp. 65-72; Oct. 26-29, 2005.
Kramb et al,.; Considerations for using phased array ultrasonics in a fully automated inspection system. Review of Quantitative Nondestructive Evaluation, 2004 Edition, ed. D. O. Thompson and D. E. Chimenti, American Inst. of Physics, pp. 817-825, Mar. 2004.
Ledesma-Carbayo et al.; Spatio-temporal nonrigid registration for ultrasound cardiac motion estimation; IEEE Trans. On Medical Imaging; vol. 24; No. 9; Sep. 2005.
Leotta et al.; Quantitative three-dimensional echocardiography by rapid imaging . . . ; J American Society of Echocardiography; vol. 10; No. 8; ppl 830-839; Oct. 1997.
Li et al.; An efficient speckle tracking algorithm for ultrasonic imaging; 24; pp. 215-228; Oct. 1, 2002.
Morrison et al.; A probabilistic neural network based image segmentation network for magnetic resonance images; Proc. Conf. Neural Networks; Baltimore, MD; vol. 3; pp. 60-65; Jun. 1992.
Nadkarni et al.; Cardiac motion synchronization for 3D cardiac ultrasound imaging; Ph.D. Dissertation, University of Western Ontario; Jun. 2002.
Opretzka et al.; A high-frequency ultrasound imaging system combining limited-angle spatial compounding and model-based synthetic aperture focusing; IEEE Transactions on Ultrasonics, Ferroelectrics And Frequency Control, IEEE, US; 58(7); pp. 1355-1365; Jul. 2, 2011.
Pinghua; Optimization of Key Parameters of Phased array Ultrasonic Testing; Dalian University of Technology; Masters Dissertation; No. 7; retrieved from the internet (http://www.cnki.net); 69 pages; Jul. 15, 2012.
Press et al.; Cubic spline interpolation; §3.3 in "Numerical Recipes in FORTRAN: The Art of Scientific Computing", 2nd Ed.; Cambridge, England; Cambridge University Press; pp. 107-110; Sep. 1992.
Saad et al.; Computer vision approach for ultrasound doppler angle estimation; Journal of Digital Imaging; 22(6); pp. 681-688; Dec. 1, 2009.
Sakas et al.; Preprocessing and vol. rendering of 3D ultrasonic data; IEEE Computer Graphics and Applications; pp. 47-54, Jul. 1995.
Sapia et al.; Deconvolution of ultrasonic waveforms using an adaptive wiener filter; Review of Progress in Quantitative Nondestructive Evaluation; vol. 13A; Plenum Press; pp. 855-862; Jan. 1994.
Sapia et al.; Ultrasound image deconvolution using adaptive inverse filtering; 12 IEEE Symposium on Computer-Based Medical Systems, CBMS, pp. 248-253; Jun. 1999.
Sapia, Mark Angelo; Multi-dimensional deconvolution of optical microscope and ultrasound imaging using adaptive least-mean-square (LMS) inverse filtering; Ph.D. Dissertation; University of Connecticut; Jan. 2000.
Scabia et al.; A real-time two-dimensional pulsed-wave Doppler system; Ultrasound in medicine & biology: 26(1); pp. 121-131; Jan. 1, 2000.
Slavine et al.; Construction, calibration and evaluation of a tissue phantom with reproducible optical properties for investigations in light emission tomography: Engineering in Medicine and Biology Workshop; Dallas, TX; IEEE pp. 122-125; Nov. 11-12, 2007.
Smith et al.; High-speed ultrasound volumetric imaging system. 1. Transducer design and beam steering; IEEE Trans. Ultrason., Ferroelect., Freq. Contr.; vol. 38; pp. 100-108; Mar. 1991.
Specht et al.; Deconvolution techniques for digital longitudinal tomography; SPIE; vol. 454; presented at Application of Optical Instrumentation in Medicine XII; pp. 319-325; Jun. 1984.
Specht et al.; Experience with adaptive PNN and adaptive GRNN; Proc. IEEE International Joint Conf. on Neural Networks; vol. 2; pp. 1203-1208; Orlando, FL; Jun. 1994.
Specht, D.F.; A general regression neural network; IEEE Trans. On Neural Networks; vol. 2.; No. 6; Nov. 1991.
Specht, D.F.; Blind deconvolution of motion blur using LMS inverse filtering; Lockheed Independent Research (unpublished); Jun. 23, 1975.
Specht, D.F.; Enhancements to probabilistic neural networks; Proc. IEEE International Joint Conf. on Neural Networks; Baltimore, MD; Jun. 1992.
Specht, D.F.; GRNN with double clustering; Proc. IEEE International Joint Conf. Neural Networks; Vancouver, Canada; Jul. 16-21, 2006.
Specht, D.F.; Probabilistic neural networks; Pergamon Press; Neural Networks; vol. 3; pp. 109-118; Feb. 1990.
Stern; The basic concepts of diagnostic ultrasound. Yale-New Haven Teachers Institute; Apr. 2005.
Ucla Academic Technology; SPSS learning module: How can I analyze a subset of my data; 6 pages; retrieved from the internet (http://www.ats.ucla.edu/stat/spss/modules/subset_analyze.htm) Nov. 26, 2001.
Urban et al; Implementation of vibro-acoustography on a clinical ultrasound system; IEEE Transactions on Ultrasonics, Ferroelectrics, and Frequency Control; 58(6); pp. 1169-1181 (Author Manuscript, 25 pgs.); Jun. 2011.
Urban et al; Implementation of vibro-acoustography on a clinical ultrasound system; IEEE Ultrasonics Symposium (IUS); pp. 326-329; Oct. 14, 2010.
Von Ramm et al.; High-speed ultrasound volumetric imaging-System. 2. Parallel processing and image display; IEEE Trans. Ultrason., Ferroelect., Freq. Contr.; vol. 38; pp. 109-115; Mar. 1991.
Wang et al., Photoacoustic tomography of biological tissues with high cross-section resolution; reconstruction and experiment; Medical Physics; 29(12); pp. 2799-2805; Dec. 2002.
Wells, P.N.T.; Biomedical ultrasonics; Academic Press; London, New York, San Francisco; pp. 124-125; Mar. 1977.
Widrow et al.; Adaptive signal processing; Prentice-Hall; Englewood Cliffs, NJ; pp. 99-116; Mar. 1985.
Wikipedia; Point cloud; 2 pages; retrieved Nov. 24, 2014 from the internet (https://en.wikipedia.org/w/index.php?title=Point_cloud&oldid=472583138).
Wikipedia; Curve fitting; 5 pages; retrieved from the internet (http: en.wikipedia.org/wiki/Curve_fitting) Dec. 19, 2010.
Wikipedia; Speed of sound; 17 pages; retrieved from the internet (http: en.wikipedia.org/wiki/Speed_of_sound) Feb. 15, 2011.
Yang et al.; Time-of-arrival calibration for improving the microwave breast cancer imaging; 2011 IEEE Topical Conf. on Biomedi-

(56) References Cited

OTHER PUBLICATIONS cal Wireless Technologies, Networks, and sensing Systems (BioWireleSS); Phoenix, AZ; pp. 67-70; Jan. 16-19, 2011.
Zhang et al.; A high-frequency high frame rate duplex ultrasound linear array imaging system for small animal imaging; IEEE transactions on ultrasound, ferroelectrics, and frequency control; 57(7); pp. 1548-1567; Jul. 2010.
Zhang et al.; Synthetic-aperture based photoacoustic re-beamforming (SPARE) approach using beamformed ultrasound data; Biomedical optics express; 7(8); pp. 3056-3068; Aug. 1, 2016.
Specht et al.; U.S. Appl. No. 17/936,420 entitled “Point source transmission and speed-of-sound correction using multi-aperture ultrasound imaging,” filed Sep. 29, 2022.
Specht et al.; U.S. Appl. No. 18/250,071 entitled “Systems and methods for tissue characterization using multiple aperture ultrasound,” filed Apr. 21, 2023.
Czerwinski et al.; Detection of lines and boundaries in speckle images-application to medical ultrasound; IEEE transactions on medical imaging; 18(2); pp. 126-136, Feb. 1999.
Zhao et al.; Shear wave speed measurement using an unfocused ultrasound beam; Ultrasound in medicine & biology; 38(9); pp. 1646-1655; Sep. 1, 2012.
Call et al.; U.S. Appl. No. 18/955,146 entitled “Systems and methods for improving ultrasound image quality by applying weighting factors,” filed Nov. 21, 2024.

* cited by examiner

MULTIPLE APERTURE ULTRASOUND IMAGING SYSTEMS AND METHODS

PRIORITY CLAIM

This patent application claims priority to U.S. provisional patent application No. 63/306,936, titled "MULTIPLE APERTURE ULTRASOUND IMAGING SYSTEMS AND METHODS" and filed on Feb. 4, 2022, which is herein incorporated by reference in its entirety. This application is related to the following US Patents: U.S. Pat. Nos. 9,146,313, 9,883,848, 10,226,234, 10,064,605, and 9,668,714.

INCORPORATION BY REFERENCE

Unless otherwise specified herein, all patents, publications and patent applications mentioned in this specification are herein incorporated by reference to the same extent as if each individual publication or patent application was specifically and individually indicated to be incorporated by reference.

FIELD

This invention generally relates to ultrasound imaging and more particularly to systems and methods for using symmetric and asymmetric synthetic aperture waveforms for use with Ping Based Multiple Aperture Imaging (PMA) or computed echo tomography (CET).

BACKGROUND

In conventional ultrasonic imaging, a focused beam of ultrasound energy is transmitted into body tissues to be examined and the returned echoes are detected and plotted to form an image. While ultrasound has been used extensively for diagnostic purposes, conventional ultrasound has been greatly limited by depth of scanning, speckle noise, poor lateral resolution, obscured tissues, and other such problems.

To insonify body tissues, an ultrasound beam is typically formed and focused either by a phased array or a shaped transducer. Phased array ultrasound is a commonly used method of steering and focusing a narrow ultrasound beam for forming images in medical ultrasonography. A phased array probe has many small ultrasonic transducer elements, each of which can be pulsed individually. By varying the timing of ultrasound pulses (e.g., by pulsing elements one by one in sequence along a row), a pattern of constructive interference is set up that results in a beam directed at a chosen angle. This is known as beam steering. Such a steered ultrasound beam may then be swept through the tissue or object being examined. Data from multiple beams are then combined to make a visual image showing a slice through the object.

Traditionally, the same transducer or array used for transmitting an ultrasound beam is used to detect the returning echoes. This design configuration lies at the heart of one of the most significant limitations in the use of ultrasonic imaging for medical purposes: poor lateral resolution. Theoretically, the lateral resolution could be improved by increasing the width of the aperture of an ultrasonic probe, but practical problems associated with increased aperture sizes have kept apertures small. Unquestionably, ultrasonic imaging has been very useful even with this limitation, but it could be more effective with better resolution.

Synthetic aperture imaging has long been utilized in ultrasound imaging. The benefits of utilizing segments of an array to image from multiple separate spatial locations and directions include enabling a "wider" areal and angular field of view that can facilitate the ultrasound illumination of and reception from otherwise difficult to access regions as well as improved image resolution quality. The ultrasound reflection data from the different segments of the array can then be stitched together into a single ultrasound image by beamforming it separately or together, or combinations thereof.

Similarly, transmissions into the imaged medium are received at subsequently different times. The longer the wait before data collection, the deeper the field of view. Therefore, one or more transmissions from the array could lead to several data collections that could be combined in memory and used to display a synthetic image or view by stitching the beamformed images from temporally separated data segments together. Usually the transducer (sometimes referred to as probe) contains an array of transmitter/receiver/transceiver elements arranged in and directed within a plane. This is usually referred to as a 1D array and is used to view a plane in the imaged medium. The element array may be straight and "linear," or arranged in a symmetric convex shape, referred to in the industry as "curvilinear" or in a convex curve. The transducer may also contain a square or rectangular array where the piezoelectric elements are arranged immediately adjacent to each other in both the height and width dimensions, also referred to as a matrix with the elements directed normal to the plane or surface containing the elements. For instance, a matrixed array could contain 256 elements that is 16 elements high by 16 elements wide. The transducer element matrix is often "cut" out of a sub-straight of piezoelectric materials or formed in a MEMS manufacturing process to construct a formation of Piezoelectric Micro-Machined Ultrasound Transducers (pMUT) or Capacitive Micro-Machined Ultrasound Transducers (cMUT).

Significant improvements have been made in the field of ultrasound imaging with the creation of multiple aperture imaging, examples of which are shown and described in Applicant's prior patents and applications. Multiple aperture imaging methods and systems allow for ultrasound signals to be both transmitted and received via separate apertures.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

SUMMARY

Figure 1:
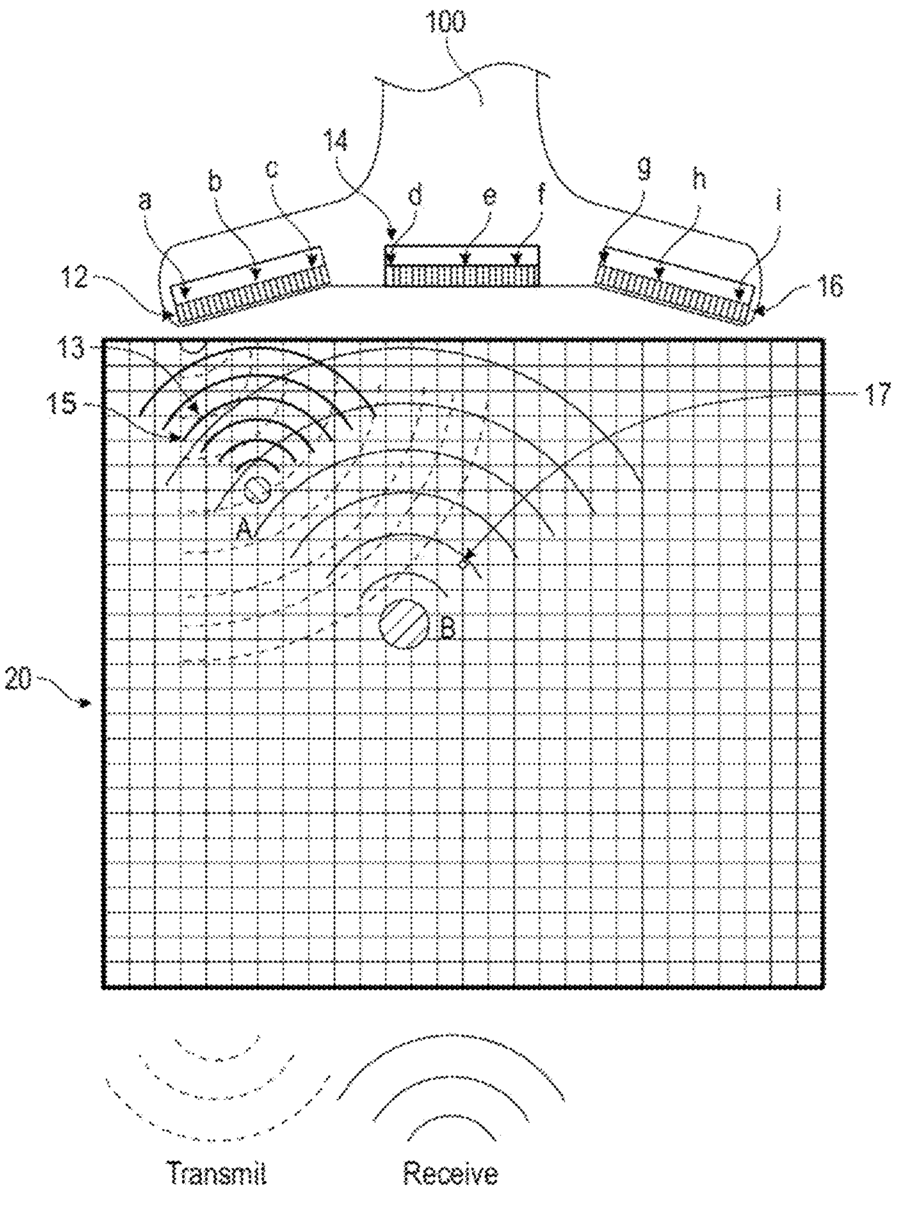
FIG. 1 is a schematic illustration of a multiple aperture imaging probe with three transducer arrays and several points to be imaged.

A method of imaging an object with ultrasound energy, the method comprising the steps of: transmitting an unfocused and diverging ultrasound signal into a target medium from an apparent point source located aft of a concave probe surface; receiving echoes from a reflector in the target medium with an omnidirectional receive element that is different than the apparent point source; determining a position of the reflector within the target medium by obtaining element position data describing a position of the spherical center point of the apparent point source r and a position of the receive element, calculating a total path distance as a sum of a first distance between the spherical center point and the reflector and a second distance between the reflector and the receive element, and determining a locus of possible points at which the reflector may lie; and producing a data set for the entire target medium.

In some aspects, the receive elements of the probe are comprised of a shell of piezoelectric material shaped as a concave curve wherein the position of the receive element is a position on the curved shell.

In one aspect, the shape of the concave probe may be either symmetric or asymmetric.

In one aspect, the probe is made of piezoelectric, cMTU or pMUT materials in a concave shape.

In one aspect, the elements or arrays of the probe are not physically attached.

In one aspect, the elements of the probe are arranged in a sparse and non-linear pattern.

In one aspect, the array or arrays of elements are shaped in 3 dimensions around two or more axes.

In one aspect, the array of elements is contained in a flexible material that may move or articulate around two or more axes.

In one aspect, the method further includes repeating the receiving, determining and producing steps with a plurality of receive elements.

In one aspect, the method further includes where a plurality of receive elements may be used to combine data for a common receive aperture.

In one aspect, the method further includes repeating the receiving, determining and producing with the elements of a plurality of receive apertures.

In one aspect, less than 10 transducers are used together to transmit the un-focused and diverging ultrasound signal.

A method of imaging an object with ultrasound energy, the method comprising the steps of: transmitting a focused and converging ultrasound signal into a target medium to an apparent point source located forward of a concave probe surface; receiving echoes from a reflector in the target medium with an omnidirectional receive element that is different than the apparent point source; determining a position of the reflector within the target medium by obtaining element position data describing a position of the spherical center point of the apparent point source and a position of the receive element, calculating a total path distance as a sum of a first distance between the spherical center point and the reflector and a second distance between the reflector and the receive element, and determining a locus of possible points at which the reflector may lie; and producing a data set for the entire medium.

In one aspect, the receive elements of the probe are comprised of a shell of piezoelectric material shaped as a concave curve wherein the position of the receive element is a position on the curved shell.

In one aspect, the shape of the concave probe may be either symmetric or asymmetric.

In one aspect, the probe is made of piezoelectric, cMTU or pMUT materials in a concave shape.

In one aspect, the elements or arrays of the probe are not physically attached.

In one aspect, the elements of the probe are arranged in a sparse and non-linear pattern.

In one aspect, the array or arrays of elements are shaped in 3 dimensions around two or more axes.

In one aspect, the array of elements is contained in a flexible material that may move or articulate around two or more axes.

In one aspect, the method further includes repeating the receiving, determining and producing steps with a plurality of receive elements.

In one aspect, the method further includes where a plurality of receive elements may be used to combine data for a common receive aperture.

In one aspect, the method further includes repeating the receiving, determining and producing with the elements of a plurality of receive apertures.

DETAILED DESCRIPTION

The various embodiments will be described in detail with reference to the accompanying drawings. References made to particular examples and implementations are for illustrative purposes and are not intended to limit the scope of the invention or the claims.

Although the various embodiments are described herein with reference to ultrasound imaging of various anatomic structures or implanted medical devices, it will be understood that many of the methods and devices shown and described herein may also be used in other applications, such as imaging and evaluating non-anatomic structures and objects.

The present disclosure describes the use of synthetic ultrasound transmit waveforms to the transducer elements that collectively generate favorable ultrasound profiles in the imaged medium in conjunction with ping-based Multiple Aperture Ultrasound (MAUI) transducers used for Computed Echo Tomography (CET). MAUI transmits focused or unfocused pings into the medium and enables reception on multiple elements that may or may not be part of a contiguous array. CET, unlike conventional phased array ultrasound systems, can use transmissions from only a small number of transducers. It can use as many transducers as desired for focused or convergent transmissions; however, unfocused or divergent transmissions do not require many transducers to form the unfocused wave. Often less than 10 transducers are used together to from a focused or unfocused transmission. This weaker signal, when combined with the other methods used in CET enable imaging tissues types that have varying speeds of sound and attenuation.

The methods of focused and unfocused transmission used in CET enable many type of probe configurations. MAUI transducers are often concave, and can be asymmetric or adjustable in one or more directions. Probes can be adjustable or even made of a pliable or mesh material. Linear or matrixed arrays can be used with CET; however, concave configurations of MAUI probes often provide better data and associated imaging do to proximity with the target and access to tissues along differing viewpoints along the probe face relative to the target medium. The methods of CET or as it's also known Ping Based Multiple Aperture Imaging (PMA) is explained in U.S. Pat. No. 9,220,478, which also demonstrates the use of several types of concave, 3D and adjustable ultrasound element array transducers and probes.

This disclosure, then, provides and describes the use of synthetic aperture transmission and reception in PMA using concave, 3D and adjustable or mesh arrays. Significant advantages in imaging capability and quality result from using either divergent, convergent directed ultrasound wavefronts or a combination of these to generate an ultrasound image.

This disclosure provides implementation and operation in an ultrasound imaging system that is provided with the necessary hardware features to transmit designed ultrasonic wave pulses/pings or sequences of pulses/pings by synthesizing and applying appropriate electrical signals to appropriate elements in the probe/array. Further this disclosure demonstrates the utilization of received ultrasound reflections from the imaged medium and how to buffer and process the transduced ultrasound reflection data using calculations outlined in the prior work. CET data sets can be used to form images for a user or analyzed without image formation with artificial intelligence as described in PCT/US2020/056652. This includes variations/enhancements of this method or using other beamforming methods. The calculations to process the received reflection data to render the ultrasound image may be performed using computer software running locally on the system or operating on a remote system or using firmware or electronic hardware.

The invention will be used improve the image quality that can be obtained with synthetic aperture ping-based imaging using 2D or 3D convex, concave, or linear segmented arrays or flexible array probes though not limited to these probe designs. The invention enables the harnessing of multiple transmit elements to generate stronger ultrasound transmits/pings and the tailoring and direction of the transmit energy of these pings to improve image quality. Improvements in image resolution, contrast signal to noise ratio, contrast to noise ratio, image field size, imaged depth and image speed are feasible using multi-element transmit through judicious selection of transmit combinations.

Examples include directing ultrasound energy using convergent wavefront transmits to improve image quality at larger depths, directing divergent wavefronts to regions of interest to image the region from multiple angles, using wide area divergent pings to speed the imaging process and locating and steering the transmits to avoid ultrasound disrupting/attenuating features in the image field to improve the image in their lee. Imaging different portions of the body or viewing these from desired viewing angles may require the use of different transmit pings or combinations of pings used to generate images.

In operation, a MAUI or PMA ultrasound imaging system will be programmed to transmit a series of pings that may vary in the location of source, divergence, extent, and direction by applying excitation voltage signals to the selected transmit element with appropriate delays to generate the desired ultrasound wavefronts. Each ping and the associated received echoes on all selected channels create a data set or string for that channel. Channel data can be combined to create a larger data set of the imaged medium. This larger data set then takes advantage of channels having differing views of the medium. Methods for solving speed of sound variations so that these data sets can be combined or discussed in prior works. The received reflection data from a series of pings will be used to generate a data set frame by processing it with the ping-appropriate beamforming calculations. All or a portion of the data set can be selected by the end user for presentation as an image. The data from the individual transmits/pings may be weighted when generating a final image frame to equalize (or enhance) differences in transmit/ping energy. Images generated from different combinations of pings may also generated in succession for display or averaging based on image requirements with or without weighting factors applied to the images.

This disclosure provides the use of multiple elements that may or may not straddle multiple arrays or segments of a multi aperture probe or a variable geometry probe to generate transmissions of strong convergent or divergent directed ultrasound waves over all or subregions of the imaged medium/field that are sufficiently uniform over that subregion to enable the generation of good ultrasound images.

Additionally, this disclosure provides for the combination and subsequent stitching of data acquired through multiple such transmissions into a single data set or single image frame.

In some embodiments, the judicious choice and design of such transmissions is provided so as to adequately cover the region of interest whilst avoiding intervening obstructions that may reduce image quality.

Additionally, weighting factors may be used to (de) emphasize stronger ping/transmit data in image beamforming.

The application of these techniques enables the acquisition of images with better quality (resolution contrast, signal to noise ratio, contrast to noise ratio) and at larger depths using multiple aperture ping technology in the medium than feasible with real point source (single element) ultrasound transmissions. These techniques can also be used to similarly enhance the image quality in otherwise obscured (by strong absorbers/reflectors) portions of the image through a judicious design of ping/transmit patterns with or without the use of appropriate weighting factors with these transmits.

Differing combinations of convergent and divergent transmissions are likely more effective with specific types of tissue and anatomical features and optimized transmission sequences can be designed and used to image different target organs and views to generate the best image of the region of interest from the selected viewing/imaging angle. For instance, imaging through the skull may require more divergent imaging and imaging into the lung may require more convergent imaging.

Ping-Based Multiple Aperture Imaging

Some embodiments of the systems and methods described herein are based on a unique imaging modality referred to as Ping-Based Multiple Aperture imaging ("PMA" imaging). An introductory description of PMA is provided below. Additional details, examples, embodiments, and applications of methods and structures useful in performing ping-based multiple aperture imaging are described in Applicant's prior patent applications referenced above.

Briefly, PMA imaging involves transmitting a series of un-focused two-dimensional or three-dimensional "pings" into a medium from a "transmit aperture" (which may be made up of one transducing structure or a group of transducers operating in concert) then receiving and storing signals produced by echoes and/or through-transmissions of each ping. Signals are received by many "receive elements" (each made up of one or more transducing structures) which may be grouped into "apertures." The receiving transducers produce time-varying analog signals with amplitudes proportional to an intensity of energy impinging on the transducer. Such analog signals may be digitally sampled at a sampling rate, and digital samples may then be stored. The value of each digital sample may be proportional to the intensity of received ultrasound. Each digital sample may represent an "echo" of some reflective or transmissive structure in the medium. Digital samples received by a single receive transducer element may be organized in "strings" of data samples, which may be sub-divided into "sub-strings" as described in some embodiments herein. An image may be formed by mapping the samples to locations within the imaged medium and assigning brightness (and/or color) values to each image point (e.g., a pixel or voxel) in proportion to the value of contributing data samples.

While terms such as "bright" and "dark" are used herein to refer to image points and data samples, the skilled artisan will recognize that such terms are not absolute, as the brightness or contrast of a displayed image may be adjusted. Instead, the terms are used in a relative sense to distinguish those data samples and image points representative of highly reflective or "echogenic" structures which are typically but not necessarily referred to as being more "bright" than minimally-reflective structures which are typically but not necessarily referred to as "dark." Of course, some imaging systems may be configured with an opposite convention in which samples with greater energy intensity are displayed as dark points while samples with less energy intensity are displayed as brighter points. In either convention, in the context of the systems and methods described herein, the term "bright" is intended to refer to points representing points of greater received energy intensity (regardless of whether the energy is received after reflection from or transmission through an imaged structure), while "darker" points are those with relatively lower received energy intensity.

Beamforming Images in from Ping Based Multiple Aperture Imaging Systems

A complete sub-image of the medium may be obtained from signals produced by each receive element. Sub-images obtained from elements of a common aperture may be combined with one another to produce a "first-level" image. Sub-images and/or first-level images from multiple ping-transmissions (transmitted from the same or different transmit apertures) may be combined to produce "second-level" images. Second-level images from multiple receive apertures may be combined to produce "third-level" images. Many permutations of image-layer combination sequences are possible and therefore sub, first, second, and third level images need not necessarily be formed in the sequence implied by the names.

If the transmit elements and/or the receive elements are spaced from one another in two or three dimensions, the "images" (including sub-images) may be three-dimensional volumes made up of three-dimensional voxels. Any two-dimensional section of such a volume may be selected and displayed as a matrix of two-dimensional pixels. The term "image point" will be used to refer to discrete elements (e.g., pixels or voxels) of a two-dimensional or three-dimensional image.

As signals are received by a transducer element, the signals may be converted into a sequence of digital data, which may be stored in a volatile and/or non-volatile memory device. Each entry in such a sequence of data entries may be referred to as a "data sample". The term "data sample" may also refer to values obtained by aggregating multiple data entries (e.g., averaging, taking a minimum or a maximum, etc.) or values obtained by interpolating between two or more data entries.

In order to form a sub-image from a collection data samples, each sample (individually, aggregated, or interpolated) must be mapped to its possible location within the image through a process referred to herein as "beamforming." Each data sample represents a range of potential locations (a locus) within the image determined by the location of the transmit element and receive element, the difference in time between ping transmission and signal reception, and the speed-of-sound through the imaged medium.

In a multiple aperture imaging system in which the transmitter is located at a different point than the receiver, the locus of possible locations for each sample takes the shape of a two-dimensional ellipse or a three-dimensional ellipsoid with the transmit element and the receive element located at the foci of the ellipse or ellipsoid reference U.S. Pat. No. 9,146,313 titled "Point Source Transmission and Speed-of-Sound Correction Using Multiple-Aperture Ultrasound Imaging. The term "locus" (and its plural "loci") will be used to refer to either an ellipse or an ellipsoid. The imaging system converges on the correct location of each image point by adding together multiple data samples with loci intersecting the same image point. Each data sample contributing to a single image point may be referred to as a "contributor" to that image point. The point at which the ellipses or ellipsoids intersect is reinforced (i.e., has a greater total brightness than its individual contributors) and represents the correct location of the point to be displayed or recorded.

This process is susceptible to a unique form of error referred to herein as neighbor noise. If a particular data sample contains a high degree of noise causing its locus to be substantially brighter than other contributors to an image point, a larger region of the neighbor noise sample may be displayed, creating a noise artifact in the shape of the locus. Such individual neighbor noise samples may create significant distortions of an image by highlighting regions that do not correspond to physical structure in the imaged medium. Distortions caused by neighbor noise may be identified through any of a number of techniques, some of which are described below. Once identified, neighbor noise can be minimized when forming an image by one or more of the techniques described herein.

Identifying Neighbor Noise Data Samples by Averaging

Highly echogenic reflectors that are substantially brighter than other contributors to the same image points are a problem that can cause neighbor noise. Here a "too bright" contributor that is overwhelming other contributors may create bright artifacts or other false information. This is particularly problematic for image points that would otherwise be relatively "dark" but-for the strong echogenic reflector located in the data samples. In an opposite but related fashion, less-echogenic reflectors can be erroneously displayed as much darker than expected because other contributors to the same image point will tend to cancel the effects of a "too dark" contributor. In both cases therefore, it may be beneficial to identify data samples (or ellipses) representing neighbor noise.

In general, for a single image point, data samples resulting from different combinations of transmitted ping and receive element may reveal brighter or darker echoes of a reflector due to differences in path length, look angle, obstacles, materials, time of ping transmission, or other factors. Nonetheless, under normal conditions, the degree of such variations can be expected to remain within predictable ranges which may be determined based on empirical testing and/or mathematical modeling/simulation. Echo values that fall significantly outside of such expected ranges are likely to be noise or other forms of error. Therefore, it may be desirable to systematically define "abnormally bright" values, identify data samples contributing "abnormally bright" values to any image point, and to minimize the deleterious impact of such abnormally bright samples.

In some embodiments, instead of evaluating every image point within the medium for high noise, the set of image points to be evaluated may be reduced to a candidate set of image points. For example, in some embodiments image points with brightness values less than a predetermined value (e.g., ≤0.9 on a scale of 0.0 to 1.0) may be selected for analysis to detect neighbor noise contributors. In other embodiments, image points with brightness values greater than a predetermined lower value (e.g., 0.1 on a scale of 0.0 to 1.0) but less than a predetermined upper value (e.g., 0.8) may be selected for analysis to detect neighbor noise contributors.

In some embodiments, image points to be evaluated for the existence of neighbor noise data samples may be identified based on an analysis of adjacent image points, or image points within a region. For example, if after applying all contributors, a particular image point has a brightness value substantially higher than all adjacent image points or all image points within a region, that image point may be selected for evaluation of contributors as possible neighbor noise contributors. In other embodiments, an image point to be evaluated for the existence of neighbor noise data samples may be identified by evaluating data samples contributing to a group of image points in a region so as to detect an "edge" between relatively darker and lighter image points in the region. An example of such a process is described in the section below.

Whether evaluating all image points or a sub-set of image points selected by a method such as those described above, various processes may be used for identifying neighbor noise contributors to a particular image point. In one example embodiment, such a process may comprise transmitting a ping from a transmit aperture, receiving reflected and/or transmitted signals from the ping, digitizing and storing sampled digital data representing the received signals, and beamforming the stored data to map data samples to image points. Then for each image point to be evaluated: determining an aggregate value of the set of data samples contributing to the image point, and identifying neighbor noise contributors as those data samples with values varying from the aggregate value by greater than an expected variance.

In various embodiments, the step of evaluating data samples to identify neighbor noise contributors may be performed before and/or after various coherent or incoherent summation steps as described in the various applications referenced above and incorporated herein by reference. For example, in some embodiments, raw data samples may be evaluated before any data summation steps in order to detect edge regions or other distinguishable features with a much greater degree of detail than may be possible after data summation.

In various embodiments, the "aggregate value" of a set of data samples contributing to a particular image point may be the arithmetic mean (simple average), median (the midpoint of all values of samples in the set), the mode (the most frequent value in the set), the maximum (the largest value of the set), the minimum (the smallest value of the set) or other value describing or obtained from the set of data samples.

In various embodiments, the variance from an aggregate value defining a neighbor noise data sample may be defined in numerous ways. For example, the variance may be a fixed numerical value, a multiple of the aggregate value, a percent change from the aggregate value, a number of standard deviations above the aggregate value, a percentile of the set of data samples contributing to the image point, or other metrics of variance from the aggregate value.

In some embodiments, neighbor noise contributors to an image point may be defined as samples with brightness values at least N times greater than the mean, median, mode, maximum, or other aggregate value of the set of contributors to the image point. In such embodiments, N may be at least about 1.0 up to about 2.0 or more.

In other embodiments, neighbor noise contributors may be defined as samples with brightness values more than N standard deviations greater than the mean value of contributors to the image point. In other embodiments, neighbor noise contributors may be defined as samples with brightness values greater than the maximum value of the set of contributors, or N times the maximum, or more than M % greater than the maximum. In other embodiments, neighbor noise contributors may be defined as samples with brightness values greater than the N times the mode, where the "mode" is defined as the most frequently occurring value in the set of data samples contributing to the image point. In some embodiments, the mode may be determined based on rounded values of the data samples (e.g., by rounding each value of the set to a predetermined number of digits and then determining the most frequent value).

Convergent and Divergent Beamforming in Ping Based Multiple Aperture Imaging

In some embodiments, mathematical or other evaluations of the raw data samples collected by multiple transducer elements from a PMA system may be done before image beamforming in order to identify data samples to be adjusted. In some embodiments, such pre-beamforming evaluation may be used for other analyses such as object recognition or others.

FIG. 1 demonstrates a ping based multiple aperture probe 100 against a skin surface S, with arrays 12, 14, and 16. Subarrays or often individual elements within each array are indicated as points a, b, c, d, e, f, g, h and i. However, sub-arrays can be located across physical gaps between arrays and should not be considered limited to individual elements on an individual array. A ping transmission is represented by the wavefront 13 (dashed wavefront(s)) generated by a transmit aperture at 'a' on array 12 and is indicated by wavelets. Point A in the medium or tissue 20 is meant to represent a hard structure (e.g., calcium or hardened plaque from atherosclerosis, or other hard objects such as bone), which would immediately reflect or scatter the transmitted wavefront 13 in multiple directions represented here as reflected wavefront 15 (solid wavefront(s)). The reflected wavefront emanating from point A may provide a relatively bright signal to the receive elements in arrays 12, 14, and 16. The transmitted wavefront 13 may also continue on through the medium or tissue 20 to point B, which is meant to represent an anechoic structure (e.g., a blood vessel or other soft tissue) that would provide a relatively weaker reflected wavefront 17 back to the elements on arrays 12, 14, and 16.

Echoes from points A and B can be received by receive elements in arrays 12, 14, and 16 and used by the probe 100 to create data sets and frames used to form multiple aperture ultrasound images or for analysis by artificial intelligence engines. An electronic controller(s) or processor(s) associated with any probe on a PMA enabled system can begin the process of analyzing the data in the region of interest. Data being collected after Analog to Digital conversion is stored into data strings for a first receiver element. This receiver element may be part of an array, or it may be an independent element used as an omni-directional receiver. It need not be used in conjunction with other elements to collect and compound data in real time. A second receiver element can be used to produce a second string of data coming off of the same ping utilized to provide receiver element data to the first receiver element. Similarly, echo data coming off of the same ping transmission can be used by a plurality of receive elements (e.g., third, fourth, fifth, etc. receiver elements).

A processor in the PMA system, in the probe itself or in communication with the probe (e.g., wirelessly) may then be configured to conduct an average of all data set values for all data strings. In some implementations, the data string may be collected for an entire region of interest (i.e., large sample period). In other implementations, the data may be collected for only a specific pixel (i.e. specific sample period). The processor can then initiate the beamforming process to create pixelated images of the region of interest. In the case of 3D imaging, the same process can be utilized to create voxel images. The process can be repeated for multiple pings and echo data strings.

Transmission of unfocused pings into the medium where the origin is not at the surface of the array, then becomes more challenging with a Ping Based Multiple Aperture Probe. U.S. Pat. No. 9,883,848 taught several techniques associated with virtual point sources. This work provides more clarification on the use of divergent and convergent beam formation using PMA and CET.

Figure 2:
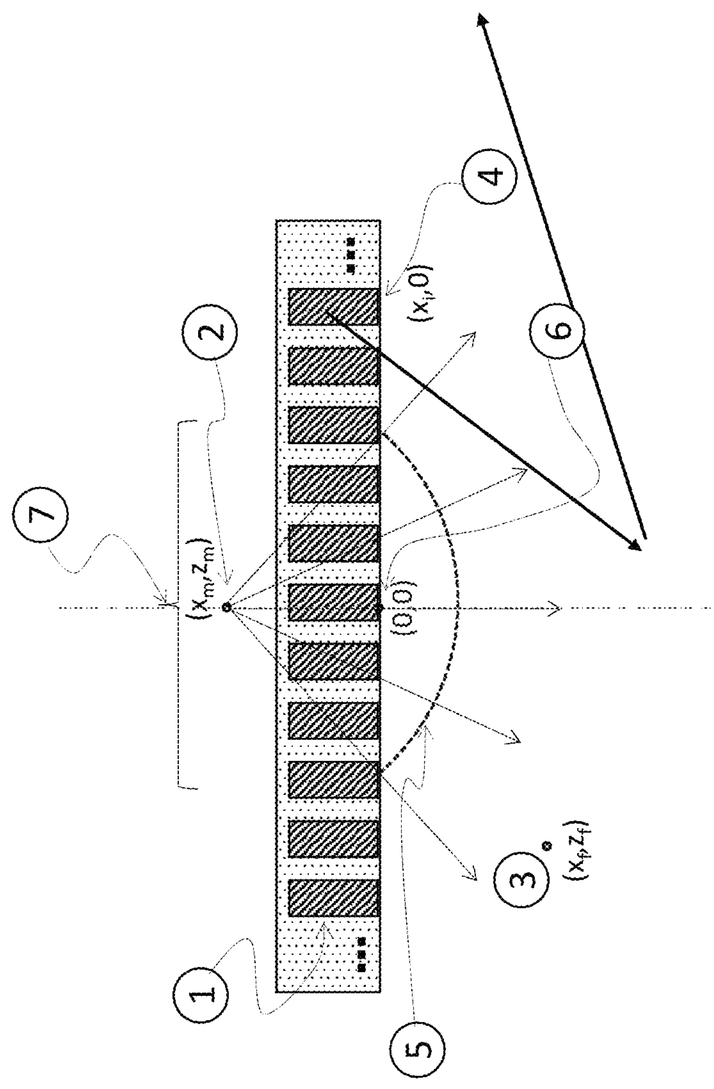
FIG. 2 illustrates divergent beam transmission with a virtual source located behind a transducer array.

To begin, FIG. 2 illustrates a transmitted ultrasound wavefront 5 generated on a conventional linear or matrixed array 1 by the application of a designed set of excitation waveforms to the transmit elements 7 of the transducer array 1. In this example, the array can include a chosen or resultant virtual point source 2 that can be located over a range of locations behind the array through proper design of the excitation waveforms. The virtual point source 2 can be configured to transmit a circular (2D) or spherical (3D) virtual transmit wave 5. If the virtual transmit wave is electronically initiated from the virtual point 2, then each of the elements of the transducer array can be controlled to fire based on a delay calculation of when the circular (2D) or spherical (3D) virtual transmit wave passes through that element. The consolidation of those firings then creates an actual physical wave into the medium with the selected virtual point source.

Figure 3:
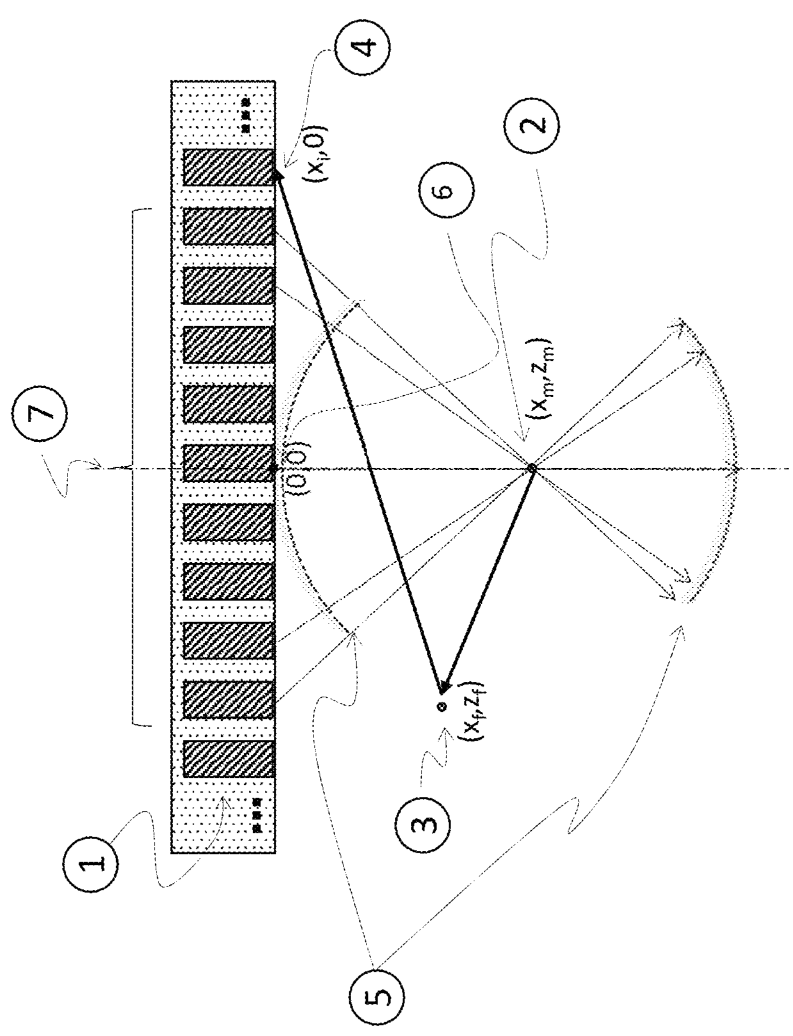
FIG. 3 shows converging or focused ultrasound waves generated by a conventional linear or matrixed array by the application of specifically designed waveforms to the transmit elements of the transducer array.

FIG. 3 shows converging or focused ultrasound waves generated by a conventional linear or matrixed array 1 by the application of specifically designed waveforms to the transmit elements 7 of the transducer array 1. Here, the virtual point source 2 (or focus) can be electronically synthesized to be any of a number of locations in front of the array 1. That is, if the pulse from each transmit element 7 were to arrive at a single location at one time, a converging circle or sphere can be constructed that would condense in size down until it hit the virtual point source 2. The time when that virtual circle or sphere 5 would pass through the transducer elements of the array 1 is when the transducer elements in the array should be fired. The coordination of those impulse firings then creates an actual physical wave into the medium which has as its target the virtual point source 2 that was selected. This enables transmissions from multiple transducers elements to be "focused" on a single point inside the medium. Echoes returning from the point source 5 are then collected by each individual receiver.

Referring to FIGS. 2-3, with a coordinate system origin 6 (0, 0), reflection time from an image field point 3 in the imaged medium with coordinates ($x_f$, $z_f$) can be calculated based on the total length of flight path from the virtual source 2 located at ($x_m$ $z_m$) to the image field point 3 ($x_f$, $z_f$) and from it to the receive element 4 of the transducer array. Knowledge of these reflection times can then be used by the system (such as with an electronic controller) to generate the image in a beamforming process. This beamforming process as well as the calculation of appropriate transducer excitation voltage waveforms require knowledge of the speed of sound in the imaged medium, commonly fixed at 1540 m/s for soft tissue. (More details can be found in U.S. patent application Ser. No. 16/506,570.)

A simple Beamforming calculation used to pixel-wise generate the ultrasound image with convergent or divergent waves for a normally directed transmission from a simple linear aperture/array is given as:

$$B(x_f, z_f) = \sum_{m=1}^{M} \sum_{i=1}^{N} s_{m,i}(\tau_{m,f} + \tau_{f,i})$$

$$\tau_{m,f} = \frac{1}{c} \cdot \left\{ \frac{\operatorname{sign}(z_m - z_f) \cdot \sqrt{(x_m - x_f)^2 + (z_m - z_f)^2} +}{\operatorname{sign}(z_m) \cdot \sqrt{H\left(|x_f| + \operatorname{sign}(z_m) \cdot L/2 \cdot \left(|x_m| + \operatorname{sign}(z_m) \cdot L/2 + z_m^2\right.\right.}} \right\}$$

with:

$$\tau_{m,f} = \frac{1}{c} \cdot \left\{ \begin{array}{c} \mathrm{sign}(z_m - z_f) \cdot \sqrt{(x_m - x_f)^2 + (z_m - z_f)^2} + \\ \mathrm{sign}(z_m) \cdot \sqrt{H\big(|x_f| + \mathrm{sign}(z_m) \cdot L/2 \cdot \big(|x_m| + \mathrm{sign}(z_m) \cdot L/2 + z_m^2} \end{array} \right\}$$

$$\tau_{f,i} = \sqrt{(x_i - x_m)^2 + (z_m)^2}$$

where:

$s_{m,i}$ is the reflected signal recorded by the $i^{th}$ receive element for the $m^{th}$ ping/transmit; $\tau_{m,f}$ is the pulse arrival time delay for a pixel located at ($x_f$, $z_f$) in the image field and $\tau_{f,i}$ is the receive time delay for the reflection from that pixel and the $i^{th}$ receive element in the probe/aperture/array; ($x_m$,$z_m$) is the location of the virtual source and is positive for a convergent or negative for a divergent transmit source; L is the width of the linear probe aperture or array and c is the mean speed of sound in the imaged medium; B($x_m$,$z_m$) is the amplitude or brightness of the beam formed image (pixel) at location ($x_f$,$z_f$); N is the number of receive elements in the probe/array/receive (sub) aperture and M is the number of different transmits/pings used to generate the image frame. H is the Heaviside step function and is equal to 0 for arguments less than or equal to zero and 1 for arguments greater than zero. The origin for the spatial coordinates is at the center of the linear array.

Figure 4:
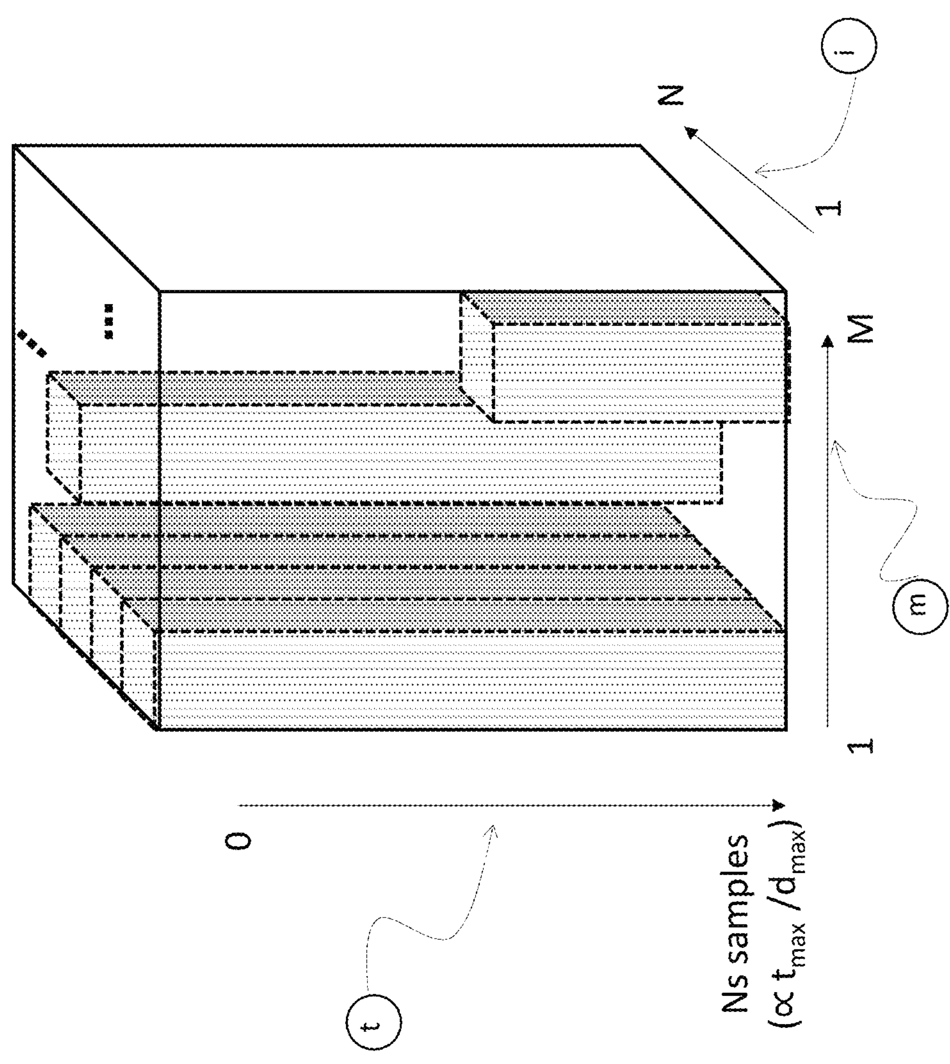
FIG. 4 is a schematic illustration of a data "cube" according to one embodiment of the present disclosure.

FIG. 4 is a schematic illustration of a data "cube" according to one embodiment of the present disclosure. The "cube" comprises reflection data acquired through a series of transmits of virtual (and/or real) sources that can be beamformed based on their individual virtual source location and summed or stitched into a single image. Different transmits can target different lateral or depth-wise spatial locations and only data pertaining to the targeted region beamformed and folded into the image. The embodiment of FIG. 4 represents the ability to assemble a data "cube" made up of samples from either divergent ultrasound waveforms, convergent ultrasound waveforms, or combinations of both. The system can receive channel data samples in time t, with the number of samples being proportional to the sampling rate and imaged depth. Samples from transmit sources/pings along index m (1 . . . M) coupled with receiver elements along index i (1 . . . N), can be coalesced from different transmits pings to create data columns within a full data "cube". The data cube (M, N, t) can then be beamformed and integrated into a single image frame.

Figure 5:
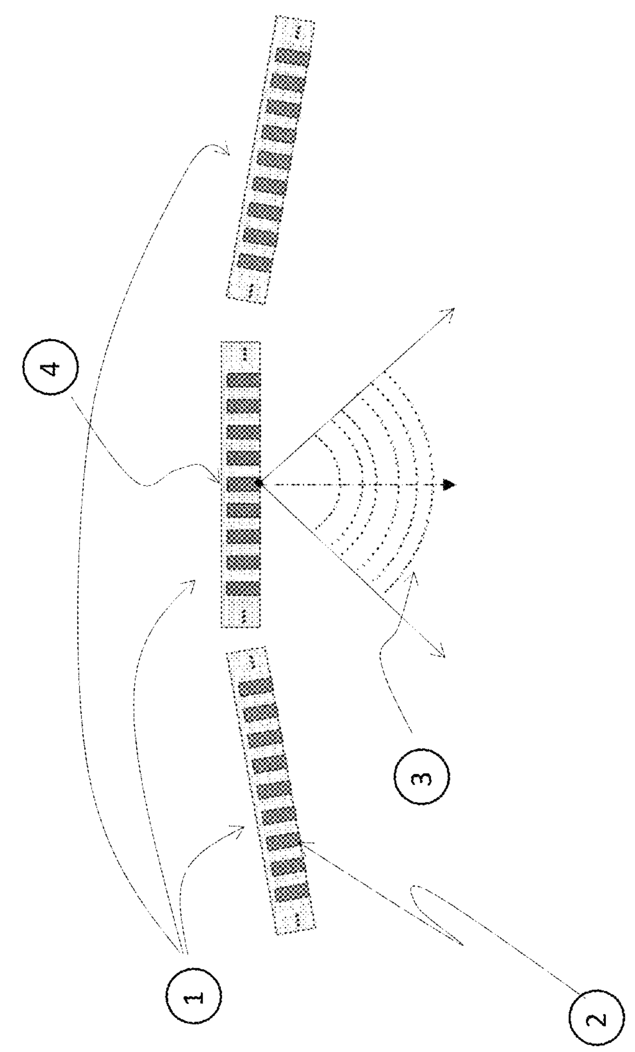
FIG. 5 shows a standard unfocused pulse being initiated from an element on a transducer array.
Figure 6:
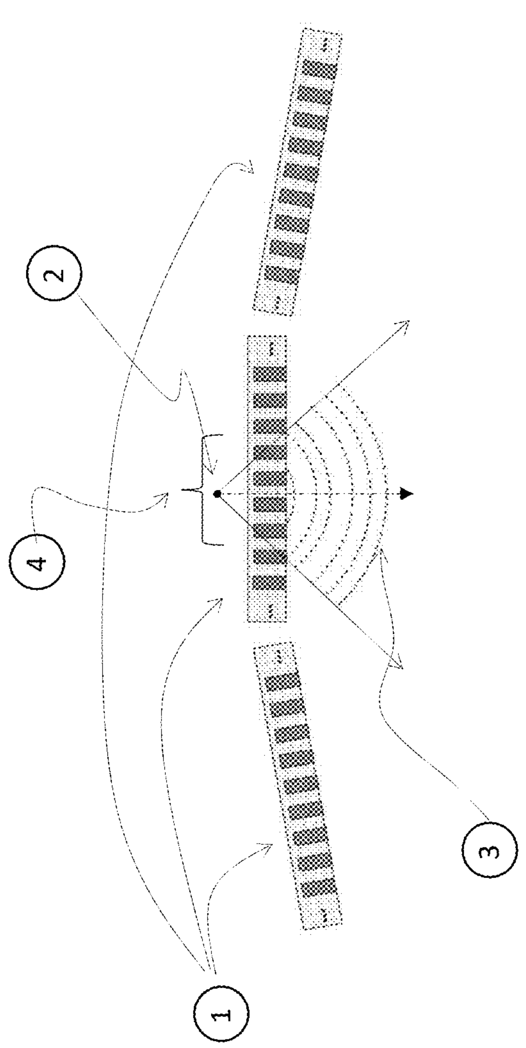
FIG. 6 shows a virtual point source behind the array could alternately or additionally be used, with elements fired using waveforms/pulses based on time delays required to create the desired semi-circular divergent or convergent wave pattern.

The techniques and methods described above can be extended to segmented or multiple aperture probes to enhance their performance. For example, FIG. 5 shows a standard unfocused pulse 3 being initiated from an element 4 on a transducer array 1. Such a pulse could come from any element 2 on any of the arrays 1. FIG. 6 progresses by showing a virtual point source 2 behind the array which could alternately or additionally be used. FIG. 6 also shows additional elements in sub-aperture 4 being fired to form waveforms/pulses based on time delays required to create the desired semi-circular divergent or convergent wave pattern.

In some embodiments the elements 4 in the arrays 1 may be cut from the same substrate. In other embodiments, the elements may be physically formed and shaped using micromachined piezoelectric materials such as Capacitive Micromachined Ultrasound Transducer (cMUT) or Piezoelectric Micromachined Ultrasound Transducer (pMUT). In these cases the element itself can be shaped to provide further benefit for the type of convergent or divergent waveforms to provide optimum imaging. For instance, a 1D array may require rectagonal shaped elements to better receive data in plane. Whereas a 2D or 3D array may require circular or elliptical shaped elements to transmit and received data from all angles. Element size, shape and location is discussed further in U.S. Pat. No. 10,586,846.

Difficulties arise in creating uniform unfocused pulses when the transmit elements for the virtual source need to span across physical separations between elements, arrays or angles due to concavity or spacing, but transmission locations and directions that require spanning such gaps may still be designed and utilized to provide the adequate wave uniformity over certain regions within the imaged medium and enabling the entire medium to be imaged without gaps. U.S. Pat. No. 10,064,605 highlights several methods used to calculate the acoustic center of each element. Element positions can be fixed based on calibration against a phantom or adjusted electronically in real time based on identification of common landmarks being imaged by multiple transducer elements. Alignment on fixed positions probes need not be done in real time or even regularly. Alignment on flexible or adjustable arrays and probes can be helpful in providing sharper imaging when using multiple aperture ultrasound imaging.

Figure 7:
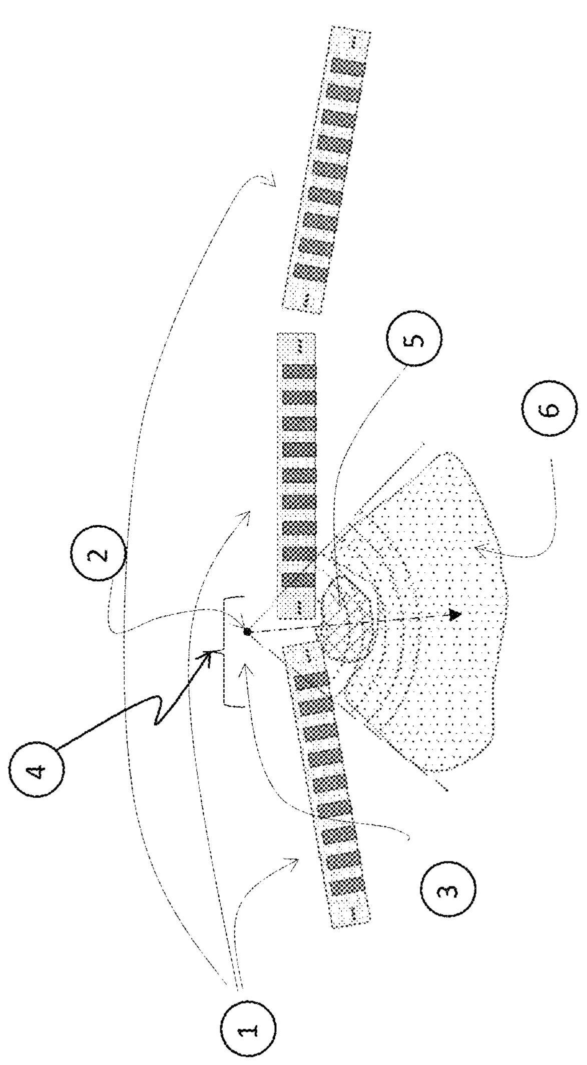
FIG. 7 illustrates how a uniform unfocused transmit waveform can be generated over specific targeted regions of the imaged medium even though there is a physical separation between arrays and a differing "view" angle caused by the concavity of the probe.

FIG. 7 illustrates how a uniform unfocused transmit waveform can be generated over specific targeted regions of the imaged medium even though there is a physical separation between arrays and a differing "view" angle caused by the concavity of the probe. When a physical separation exists between elements or arrays being utilized in a multiple aperture ultrasound probe, as shown in FIG. 7, and where the divergent virtual point source 2 is located in between or directly behind the physical separate, an "imaging dead zone" 5 may be located in the immediate near field in front of the separation. In this area, due to wave interference effects, suitable reflections may not exist to provide enough data to beamform an acceptable image, compared to the region 6 as shown which does provide good transmit pulse quality and subsequently high quality data and imaging). Shifting the virtual point source 2 to a different location 3 can serve to reduce the size of a dead zone, especially when multiple virtual point source transmissions are utilized in the collection and creation of the data set for the image. The size of the imaging dead zone may also vary based on the physical size of the separation and/or the angle of the planes of the separate elements or arrays. For instance, where there is a wide separation, but the angle between the elements or arrays is large, the dead zone may be negligible. Conversely, where the angle is almost zero, the dead zone could be as large as the separation itself. Methods described in U.S. Pat. No. 9,668,714 can then be used to applying weighting factors to data being collected and ultimately assembled in the data set and pixel/voxel.

Figure 8:
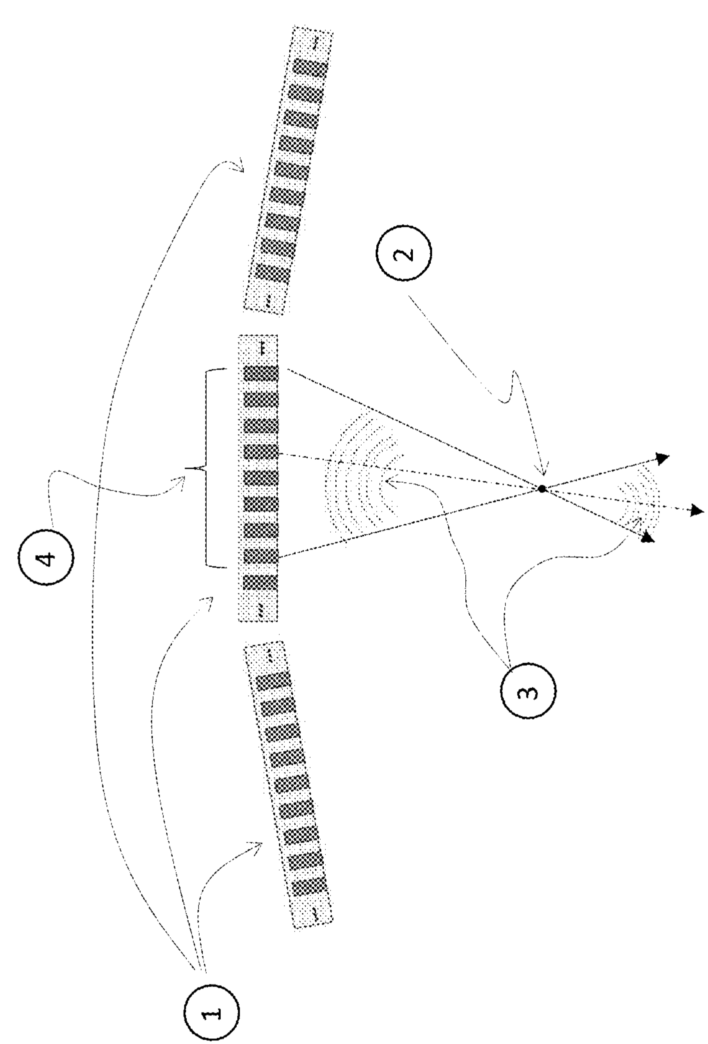
FIG. 8 illustrates a system that can include three separate arrays having transducer elements used to generate convergent waveforms to target a specific point.

In the embodiment of FIG. 8, the system can include three separate arrays 1 having transducer elements 4. As shown, waves can be generated from three different transducer elements 4 that are physically separate. Traditionally, a focal point 2 is located mostly equidistant from each element in each array. In this example, there is a similarity that the convergent waves 3 were formed from a sub-aperture 4 focused on the same point. Common convergent focal point targets could be insonified by sup-apertures of transmit elements from any of the arrays 1 in the probe as long as they are substantially equidistant. However, FIG. 8 demonstrates that the focal point need not be equidistant from each element or array. In this example, the convergent/focused wave insonified region 3 is shown bounded by the intersection of the three convergent waves. The focal point may favor one side of the targeted tissue area, as shown. This technique could then be utilized thousands of times over so that focal points would be located throughout the targeted tissue area and stitching the images from each of the targeted regions to into a single image. When imaging at larger depths using MAUI imaging, it may be necessary to only use portions of the probe to provide a transmission to the target to favor getting adequate transmission strength through to the target while avoid strong reflectors at shallow depths.

Figure 9:
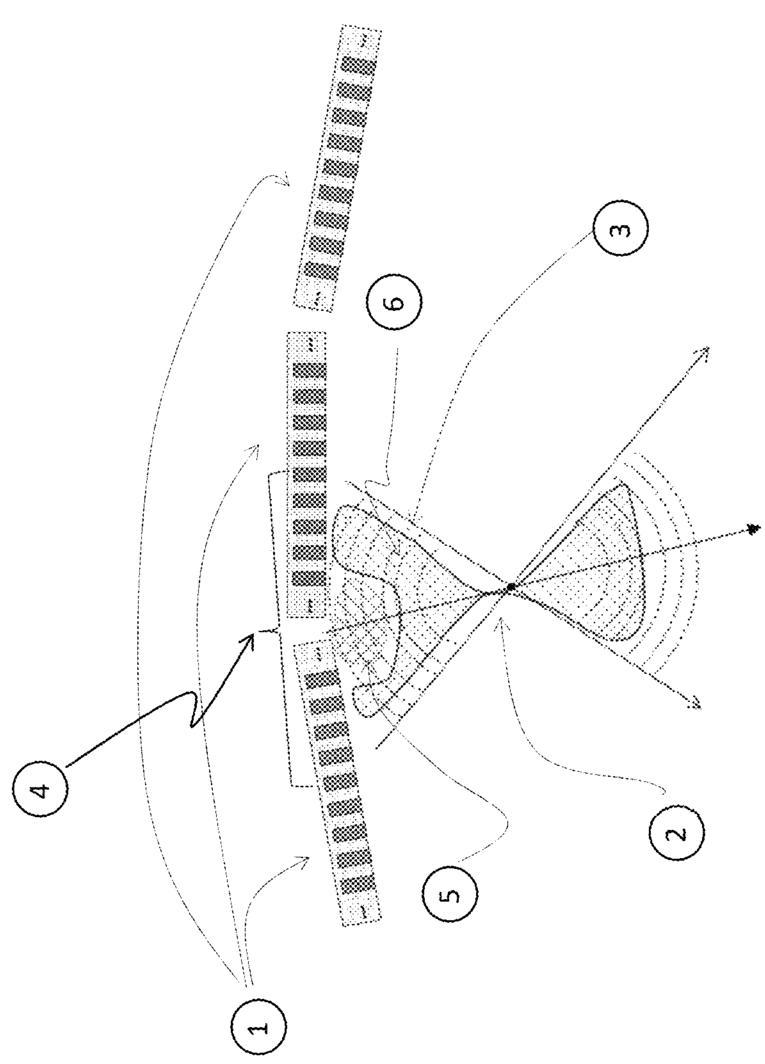
FIG. 9 illustrates convergent wave transmission using multiple elements spread across two segments of a multi segment concave probe.

FIG. 9 illustrates convergent wave transmission using multiple elements 4 spread across two segments 1 of a multi segment concave probe. In the embodiment of FIG. 9, only a portion of the multiple aperture probe is used to transmit converging energy to a deep focal target on the left side of the area of interest, resulting in a convergent/focused wave 3. The virtual point source 2 is shown. In this embodiment, region 5 illustrates an area with poor transmit pulse quality and region 6 illustrates a region with good transmit pulse quality. Shifting the virtual point source 2 to a different location inside the medium can serve to reduce the size of a dead zone, especially when multiple virtual point source transmissions are utilized in the collection and creation of the data set for the image. The size of the imaging dead zone may also vary based on the physical size of the separation and/or the angle of the planes of the separate elements or arrays. For instance, where there is a wide separation, but the angle between the elements or arrays is large, the dead zone may be negligible. Conversely, where the angle is almost zero, the dead zone could be as large as the separation itself. Methods described in U.S. Pat. No. 9,668,714 can then be used to applying weighting factors to data being collected and ultimately assembled in the data set and pixel/voxel.

Figure 10:
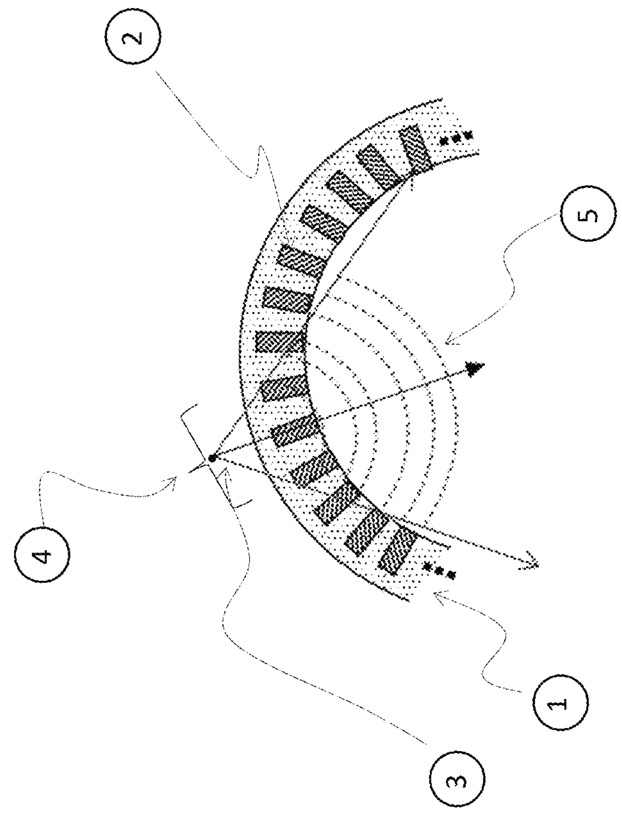
FIG. 10 illustrates an embodiment in which a smoothly curved concave transducer array including transmit elements configured to produce multiple transmissions that can cover multiple subregions within the field of interest with adequately uniform divergent waves using a proper choice of transmit array elements.

FIG. 10 illustrates an embodiment in which a smoothly curved concave transducer array 1 including transmit elements 4 configured to produce multiple transmissions that can cover multiple subregions within the field of interest with adequately uniform divergent waves 5 using a proper choice of transmit array elements 2. Multiple images can be stitched together to produce the final image. The probe need not be symmetrical. In this embodiment, the virtual point source 3 is positioned behind the array 1. Ping-based MAUI transmissions can be created that are uniform and unfocused provided that the element positions are known prior to waveform generation.

Figure 11:
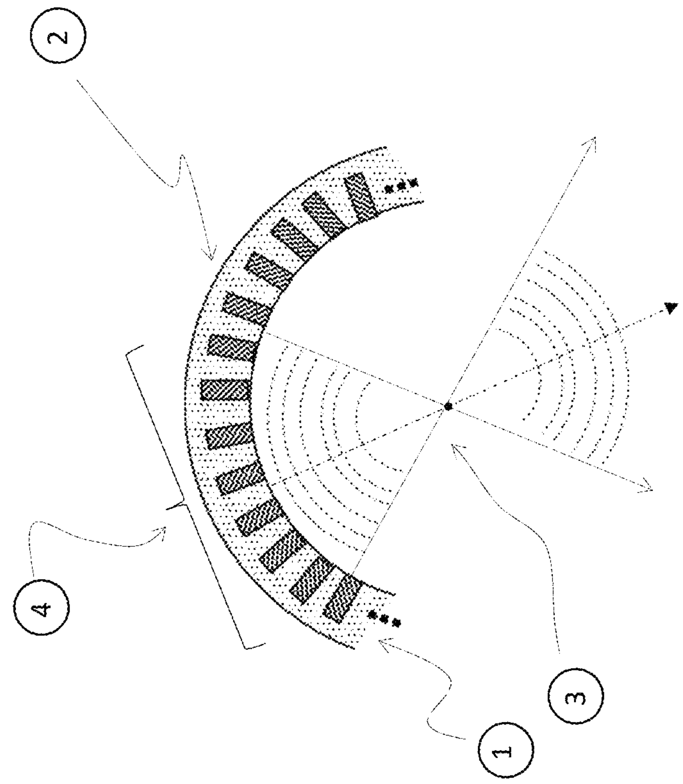
FIG. 11 shows convergent wave transmission using multiple elements within a smooth concave transducer array.

FIG. 11 shows convergent wave transmission using a subset of elements 4 from within a smooth concave transducer array 1 comprised of a larger number of elements 2. In this embodiment, a uniform convergent transmit wave can be formed from the transducer array, with a virtual point source 3 positioned at the focus (e.g., in front of the array). This probe need not be symmetrical. Ping-based MAUI transmissions can be created that our uniform and converging provided the element positions are known prior to waveform generation.

Figure 12:
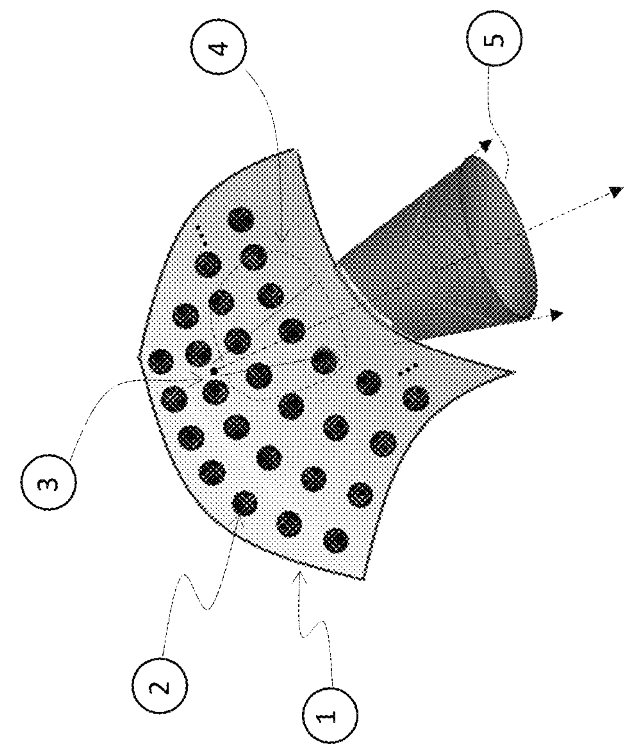
FIG. 12 shows an embodiment of divergent wave transmission using multiple transducers from an array within a 3D curved probe with a 2D transducer array module.
Figure 13:
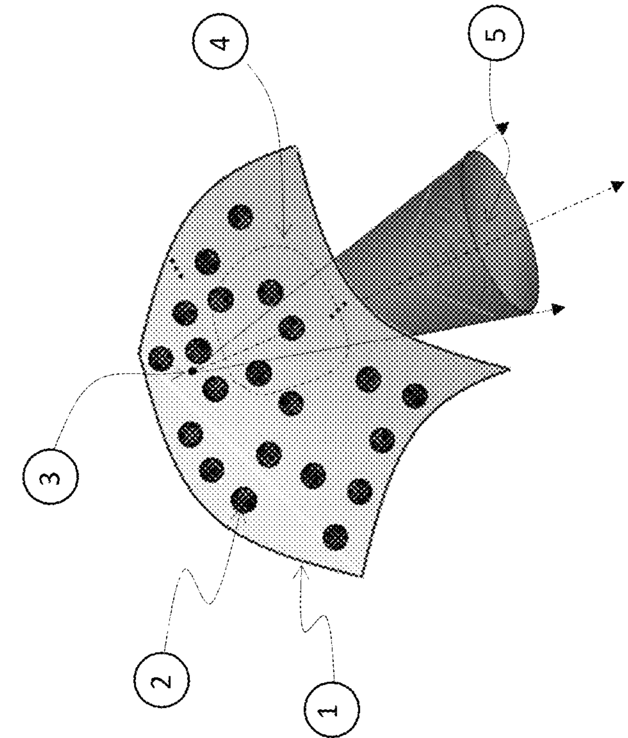
FIG. 13 shows a similar embodiment to that of FIG. 12, except the transducer array comprises a sparse transducer array.

FIG. 12 shows an array 1 that has transducers located in an array that is curved around multiple axes into a concave shape. In some embodiments, a flat 2D rectangular transducer could be used to the same effect. These arrays are described more fully in U.S. Pat. No. 10,835,208. This embodiment may be used to create a divergent wave transmission by using multiple transducer elements 2 from the array 1. Further, the array 1 need not be fixed or static. It can be adjustable or a flexible mesh. Calibration of such adjustable arrays is described in U.S. Pat. No. 9,510,806. 3D curved probe 1 can be constructed in multiple ways. In one embodiment, the 3D probe may be made of multiple flat segments of 2D planar arrays to approximate the 3D curvature. In another embodiment, a custom curved array can be constructed using cMUT or pMUT transducer in a shaped substrate. The transducer array 1 can be configured to generate ultrasound wavefronts, as described herein. In the illustrated example, a subgroup 4 of transmit elements 2 are configured to generate a divergent wave with a virtual source point 3 located behind the transmit elements, resulting in an insonified region 5 as shown. FIG. 13 shows a similar embodiment to that of FIG. 12, except the transducer array comprises a sparse transducer array 2. PMA systems using Computed Echo Tomography do not require elements to be adjacent to each other or even in the same plane. Elements need not be in the same arrays, but their positions must be known as described in U.S. Pat. No. 9,510,806. Elements may be sparse, random, physically separated and can be out of plane with each other and still used effectively within the same PMA transmit and receive sequence. Methods related to these types of arrays are described further in U.S. Pat. No. 10,854,846.

Figure 14:
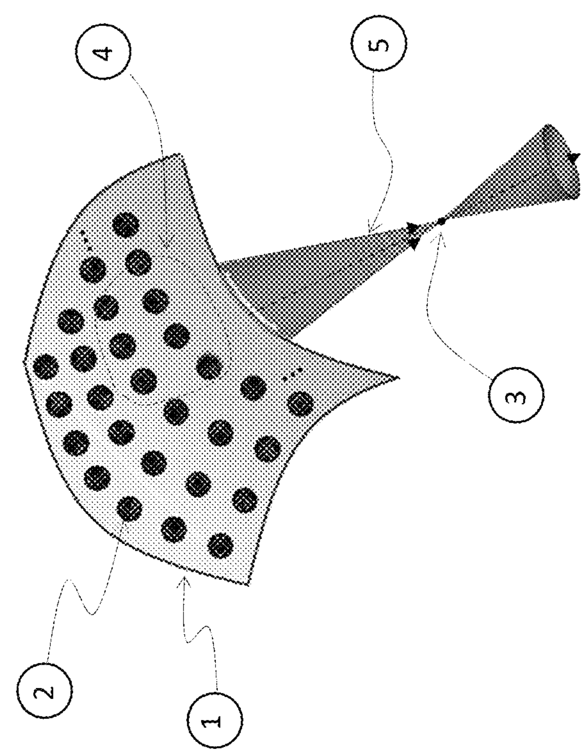
FIGS. 14 and 15 are similar to the embodiments of FIGS. 12 and 13, respectively, except they show convergent or focused wave transmission using multiple elements within a regular 3D curve probe, with a 2D transducer array (or 2D sparse transducer array).
Figure 15:
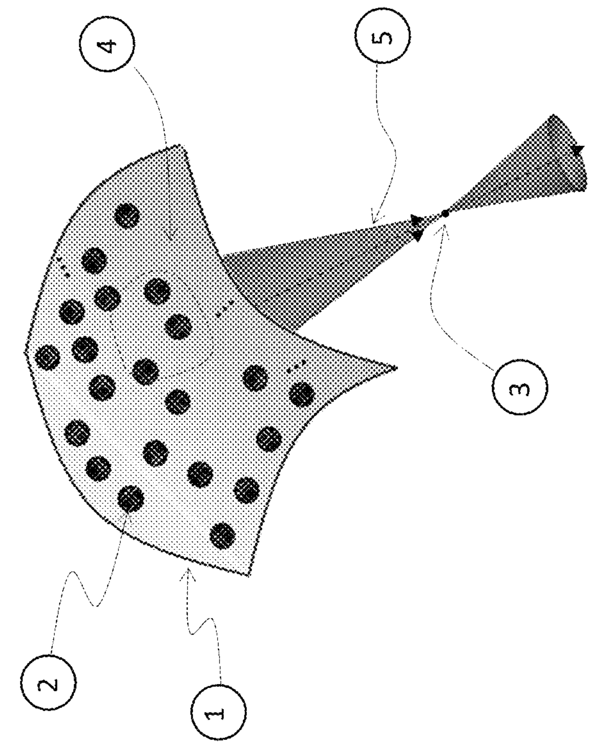

FIGS. 14 and 15 are similar to the embodiments of FIGS. 12 and 13, respectively, except they show convergent or focused wave transmission using multiple elements within a 3D curved probe array that is curved around multiple axes into a concave shape. In some embodiments, a flat 2D rectangular transducer could be used to the same effect. In these embodiments, the virtual point source 3 is located at the focal point of the transducer array, as shown, resulting in insonified regions 5 both before and after the virtual point source.

Additional geometric corrections may be required if the transmissions are directed or received in directions other than normal to the array or the geometry of the probe is not linear, but the principle of determining transmit and receive path length and time to beamform the received data into an image stands.

Regardless of the array type 1D, 2D or 3D used with a PMA system, each ping and the associated received echoes on all selected channels create a data set or string for that channel. Channel data can be combined to create a larger data set of the imaged medium. It will be understood by those familiar with the art, that using a combination of virtual point sources during transmission to include both convergent and divergent transmission and the subsequent collection and combination of channel data into a larger data set may provide optimum image quality. This larger data set then takes advantage of channels having differing views of the medium. Methods for solving speed of sound variations so that these data sets can be combined or discussed in prior works. All or a portion of the data set can be selected by the end user for presentation as an image. The data from the individual transmits/pings may be weighted when generating a final image frame to equalize (or enhance) differences in transmit/ping energy.

Any of the foregoing embodiments may be used in combination with a multiple aperture imaging probe of any desired construction. Examples of multiple aperture ultrasound imaging probes are provided in Applicant's prior patent applications referenced herein.

Embodiments of the systems and methods described above may also be beneficially applied to multiple aperture ultrasound imaging systems utilizing focused phased array transmit pulses rather than point source transmit pulses (pings). Similarly, embodiments of the systems and methods described above may also be beneficially applied to single-aperture imaging systems using multiple sub-apertures for ping transmission. In still further embodiments, the methods described above may also be applied to conventional ultrasound systems using phased array-transmissions from a single-aperture probe.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. Various modifications to the above embodiments will be readily apparent to those skilled in the art, and the generic principles defined herein may be applied to other embodiments without departing from the spirit or scope of the invention. Thus, it is intended that the scope of the present invention herein disclosed should not be limited by the particular disclosed embodiments described above, but should be determined only by a fair reading of the claims that follow.

In particular, materials and manufacturing techniques may be employed as within the level of those with skill in the relevant art. Furthermore, reference to a singular item, includes the possibility that there are plural of the same items present. More specifically, as used herein and in the appended claims, the singular forms "a," "and," "said," and "the" include plural referents unless the context clearly dictates otherwise. As used herein, unless explicitly stated otherwise, the term "or" is inclusive of all presented alternatives, and means essentially the same as the commonly used phrase "and/or." It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs.

What is claimed is:

1. A method of imaging an object with ultrasound energy, the method comprising the steps of:

transmitting an un-focused and diverging ultrasound signal into a target medium from an apparent point source located behind an array of transducer elements on a concave probe surface;

receiving echoes from a reflector in the target medium with an omnidirectional receive element in the array that is different than the apparent point source;

determining a position of the reflector within the target medium by obtaining element position data describing a position of the spherical center point of the apparent point source and a position of the receive element, calculating a total path distance as a sum of a first distance between the spherical center point and the reflector and a second distance between the reflector and the receive element, and determining a locus of possible points at which the reflector may lie; and producing one or more images of the entire target medium that includes the reflector.

2. The method of claim 1, wherein the receive elements of the probe are comprised of a shell of piezoelectric material shaped as a concave curve wherein the position of the receive element is a position on the curved shell.

3. The method of claim 2 where the shape of the concave probe may be either symmetric or asymmetric.

4. The method of claim 2 where the probe is made of piezoelectric, cMTU or pMUT materials in a concave shape.

5. The method of claim 2 where the transducer elements of the array are not physically attached.

6. The method of claim 2 where the transducer elements of the probe are arranged in a sparse and non-linear pattern.

7. The method of claim 2 where transducer elements are shaped in 3 dimensions around two or more axes.

8. The method of claim 2 where the array is contained in a flexible material that may move or articulate around two or more axes.

9. The method of claim 1, further comprising repeating the receiving, determining and producing steps with a plurality of receive elements.

10. The method of claim 1, further comprising where a plurality of receive elements may be used to combine data for a common receive aperture.

11. The method of claim 1, further comprising repeating the receiving, determining and producing with the elements of a plurality of receive apertures.

12. The method of claim 1, wherein less than 10 transducer elements are used together to transmit the un-focused and diverging ultrasound signal.

* * * * *